United States Patent
Allen

(10) Patent No.: US 11,096,756 B2
(45) Date of Patent: Aug. 24, 2021

(54) ZIP STRIP DRAPING SYSTEM AND METHODS OF MANUFACTURING SAME

(71) Applicant: Medline Industries, Inc, Northfield, IL (US)

(72) Inventor: Fred L Allen, Wonder Lake, IL (US)

(73) Assignee: Medline Industries, Inc., Northfield, IL (US)

( * ) Notice: Subject to any disclaimer, the term of this patent is extended or adjusted under 35 U.S.C. 154(b) by 396 days.

(21) Appl. No.: 16/016,326

(22) Filed: Jun. 22, 2018

(65) Prior Publication Data

US 2018/0296295 A1    Oct. 18, 2018

Related U.S. Application Data

(60) Division of application No. 13/589,640, filed on Aug. 20, 2012, now Pat. No. 10,039,610, which is a (Continued)

(51) Int. Cl.
*A61B 19/08* (2006.01)
*A61B 46/00* (2016.01)
*A61B 46/20* (2016.01)

(52) U.S. Cl.
CPC .............. *A61B 46/40* (2016.02); *A61B 46/00* (2016.02); *A61B 2046/205* (2016.02)

(58) Field of Classification Search
CPC ......... A61B 46/00; A61B 46/10; A61B 46/20; A61B 2046/205; A61B 46/23;
(Continued)

(56) References Cited

U.S. PATENT DOCUMENTS

| 371,353 A | 10/1887 | Perry |
|---|---|---|
| 842,224 A | 1/1907 | Mills |

(Continued)

FOREIGN PATENT DOCUMENTS

| CA | 2343482 | 10/2001 |
|---|---|---|
| CA | 2799116 | 8/2013 |

(Continued)

OTHER PUBLICATIONS

Opera, Karen , "Office Action", Canadian Application No. 2,847,495; dated Oct. 24, 2018.
(Continued)

*Primary Examiner* — Victoria J Hicks
(74) *Attorney, Agent, or Firm* — Philip H. Burrus, IV

(57) ABSTRACT

A medical drape has a tool-less removal feature and includes a drape material, a drape cut, an adhesive tape strip, and a scoreline. The drape material has a top side, a back side, and at least one exterior edge. The drape cut has a starting point at the exterior edge and extends completely through the thickness of the drape material. The adhesive tape strip is positioned along the length of the drape cut to overlap at least a portion of the drape material on both sides of the drape cut to initially secure the two adjoining cut edges to each other. The scoreline extends along the length of the adhesive tape strip and only partially through the thickness of the adhesive tape strip to permit easy tearing of the adhesive tape strip for separation of the two adjoining cut edges.

20 Claims, 11 Drawing Sheets

Related U.S. Application Data continuation-in-part of application No. 12/188,931, filed on Aug. 8, 2008, now Pat. No. 10,271,916.

(60) Provisional application No. 61/538,642, filed on Sep. 23, 2011.

(58) Field of Classification Search
CPC ......... A61B 46/30; A61B 46/40; A61B 46/13; A61B 2046/234; A61B 2046/236; A61B 2090/03; A61B 46/17; A61B 2046/201; A61B 46/27
USPC ........................................ 128/853, 854, 849
See application file for complete search history.

(56) References Cited

U.S. PATENT DOCUMENTS

| | | | |
|---|---|---|---|
| 850,960 A | 4/1907 | O'Connoor | |
| 884,063 A | 4/1908 | Baldwin | |
| 1,506,332 A | 8/1924 | Bloom | |
| 1,980,435 A | 11/1934 | Reagan | |
| D108,151 S | 1/1938 | Cairns | |
| 2,172,162 A | 8/1939 | Gillette | |
| 2,292,347 A | 8/1942 | Bailey | |
| D136,385 S | 9/1943 | Pons | |
| D136,386 S | 9/1943 | Pons | |
| 2,374,643 A | 5/1945 | Boettcher | |
| D146,506 S | 3/1947 | Kenny | |
| 2,430,941 A | 11/1947 | Long | |
| 2,431,466 A | 11/1947 | Barri | |
| 2,449,584 A | 9/1948 | Briton | |
| 2,556,931 A | 6/1951 | Miller | |
| 2,653,324 A | 8/1953 | McMahon | |
| 2,668,294 A | 2/1954 | Gilpin | |
| 2,673,347 A | 3/1954 | Weiss | |
| 2,825,902 A | 3/1958 | Marcus | |
| 2,971,198 A | 2/1961 | Tomich | |
| D193,132 S | 7/1962 | Rhoads et al. | |
| 313,046 A | 4/1964 | Mitchell | |
| 3,129,432 A | 4/1964 | Belkin | |
| 3,130,462 A | 4/1964 | Mitchell | |
| 3,144,661 A | 8/1964 | Buser | |
| 3,229,305 A | 1/1966 | Nevitt | |
| 3,276,036 A | 10/1966 | Carter et al. | |
| D208,527 S | 9/1967 | Grengg | |
| 3,359,569 A | 12/1967 | Scrivens | |
| 3,397,406 A | 8/1968 | Leach | |
| 3,399,406 A | 9/1968 | Bradley | |
| 3,429,433 A | 2/1969 | Holt | |
| 3,451,062 A | 6/1969 | Bradley | |
| 3,540,441 A | 11/1970 | Collins | |
| 3,625,206 A | 12/1971 | Charnley | |
| 3,696,443 A | 10/1972 | Taylor | |
| 3,707,964 A | 1/1973 | Patience et al. | |
| 3,721,997 A | 3/1973 | Mundt | |
| 3,721,999 A | 3/1973 | Goya et al. | |
| 3,750,664 A | 8/1973 | Collins | |
| 3,803,640 A | 4/1974 | Ericson | |
| 3,824,625 A | 7/1974 | Green | |
| D233,634 S | 11/1974 | Snider | |
| 3,858,243 A | 1/1975 | Pierron et al. | |
| 3,868,728 A | 3/1975 | Krzewinski | |
| 3,881,474 A | 5/1975 | Krzewinski | |
| 3,881,476 A | 5/1975 | Bolker et al. | |
| D236,293 S | 8/1975 | Banks | |
| 3,921,221 A | 11/1975 | Zoephel | |
| 3,935,596 A | 2/1976 | Allen, Jr. et al. | |
| 3,952,373 A | 4/1976 | Noorily | |
| 3,956,048 A | 5/1976 | Nordgren | |
| 3,968,792 A | 7/1976 | Small | |
| 3,989,040 A | 11/1976 | Lofgren et al. | |
| 4,000,521 A | 1/1977 | Zoephel et al. | |
| 4,017,909 A | 4/1977 | Brandriff | |
| 4,040,124 A | 8/1977 | Zoephel | |
| 4,041,942 A | 8/1977 | Dougan et al. | |
| 4,119,093 A | 10/1978 | Goodman | |
| 4,119,095 A | 10/1978 | Lewis | |
| 4,134,398 A | 1/1979 | Scrivens | |
| 4,153,054 A | 5/1979 | Boone | |
| 4,171,542 A | 10/1979 | Cox et al. | |
| D254,276 S | 2/1980 | Behrmann | |
| 4,214,320 A | 7/1980 | Belkin | |
| RE30,520 E | 2/1981 | Pierron | |
| 4,266,663 A | 5/1981 | Geraci | |
| 4,290,148 A | 8/1981 | Roberts | |
| 4,308,864 A | 1/1982 | Small et al. | |
| 4,315,334 A | 2/1982 | Pearsall | |
| 4,323,062 A | 4/1982 | Canty | |
| 4,334,529 A | 5/1982 | Wirth | |
| D267,830 S | 2/1983 | Arnseth et al. | |
| 4,384,573 A | 5/1983 | Elliott | |
| 4,397,309 A * | 8/1983 | McAllester | A61B 46/00 128/855 |
| 4,408,357 A | 10/1983 | Toth | |
| 4,467,477 A | 8/1984 | DeGennaro | |
| 4,476,587 A | 10/1984 | Itoi | |
| 4,476,860 A | 10/1984 | Collins et al. | |
| 4,479,492 A * | 10/1984 | Singer | A61B 46/00 128/853 |
| 4,489,720 A | 12/1984 | Morris et al. | |
| 4,504,977 A | 3/1985 | King et al. | |
| 4,523,335 A | 6/1985 | Scrivens | |
| 4,535,481 A | 8/1985 | Ruth-Larson et al. | |
| 4,553,538 A | 11/1985 | Rafelson | |
| 4,561,126 A | 12/1985 | Truman | |
| 4,569,341 A | 2/1986 | Morris | |
| 4,570,268 A | 2/1986 | Freeman | |
| 4,596,245 A | 6/1986 | Morris | |
| 4,616,642 A | 10/1986 | Martin et al. | |
| 4,622,699 A | 11/1986 | Spriggs | |
| 4,627,427 A * | 12/1986 | Arco | A61B 46/00 128/853 |
| 4,631,756 A | 12/1986 | Scrivens | |
| 4,653,120 A | 3/1987 | Leaf | |
| 4,664,103 A | 5/1987 | Martin et al. | |
| 4,674,132 A | 6/1987 | Stein et al. | |
| 4,686,715 A | 8/1987 | Price | |
| 4,705,171 A | 11/1987 | Eldridge | |
| 4,711,236 A | 12/1987 | Glassman | |
| 4,718,124 A | 1/1988 | Sawicki et al. | |
| 4,736,467 A | 4/1988 | Schwarze et al. | |
| 4,745,915 A | 5/1988 | Enright et al. | |
| 4,783,854 A | 11/1988 | Bjorklund | |
| 4,829,602 A | 5/1989 | Harreld et al. | |
| 4,864,657 A | 9/1989 | Lake | |
| 4,869,271 A | 9/1989 | Idris | |
| D305,376 S | 1/1990 | Russell | |
| D305,575 S | 1/1990 | Gordon et al. | |
| 4,905,710 A | 3/1990 | Jones | |
| 4,920,578 A | 5/1990 | Janzen et al. | |
| 4,942,987 A | 7/1990 | Stackhouse | |
| 4,951,317 A | 8/1990 | Gray et al. | |
| 4,951,318 A | 8/1990 | Harreld et al. | |
| 4,964,173 A | 10/1990 | Gordon | |
| 4,969,215 A | 11/1990 | Burkett | |
| 5,010,592 A | 4/1991 | Skiles, Jr. | |
| 5,027,438 A | 7/1991 | Schwarze et al. | |
| 5,029,344 A | 7/1991 | Shannon et al. | |
| 5,033,115 A | 7/1991 | Bowling et al. | |
| D319,113 S | 8/1991 | Adams | |
| 5,042,507 A | 8/1991 | Dowdy | |
| 5,061,246 A | 10/1991 | Anapliotis | |
| 5,063,919 A | 11/1991 | Silverberg | |
| 5,074,316 A | 12/1991 | Dowdy | |
| 5,088,116 A | 2/1992 | Gould | |
| 5,097,534 A | 3/1992 | Viemeister et al. | |
| 5,109,873 A * | 5/1992 | Marshall | A61B 46/00 128/849 |
| 5,135,188 A | 8/1992 | Anderson et al. | |
| 5,136,758 A | 8/1992 | Wilcox et al. | |
| 5,140,996 A * | 8/1992 | Sommers | A61B 46/00 128/849 |
| 5,143,091 A * | 9/1992 | Patnode | A61B 46/00 128/849 |

(56) References Cited

U.S. PATENT DOCUMENTS

| | | | |
|---|---|---|---|
| 5,184,351 A | 2/1993 | Benstock | |
| 5,253,642 A | 10/1993 | Stackhouse et al. | |
| 5,271,100 A | 12/1993 | Holt | |
| D348,974 S | 7/1994 | Whitwill | |
| 5,345,946 A | 9/1994 | Butterworth et al. | |
| D351,712 S | 10/1994 | Jackson | |
| 5,362,306 A | 11/1994 | McCarver et al. | |
| 5,372,589 A | 12/1994 | Davis | |
| 5,377,387 A | 1/1995 | Freed | |
| D356,204 S | 3/1995 | Derrickson | |
| 5,410,758 A | 5/1995 | Dupont et al. | |
| 5,414,867 A | 5/1995 | Bowling et al. | |
| 5,417,225 A | 5/1995 | Rubenstein et al. | |
| 5,444,871 A | 8/1995 | Lopez | |
| 5,444,872 A | 8/1995 | Johnson | |
| 5,444,873 A | 8/1995 | Levin | |
| D362,331 S | 9/1995 | Berger, II | |
| 5,454,119 A | 10/1995 | Thomm | |
| 5,533,209 A | 7/1996 | Davis | |
| D374,113 S | 10/1996 | Console | |
| 5,561,861 A | 10/1996 | Lopez et al. | |
| 5,575,006 A | 11/1996 | Wolfe | |
| 5,605,534 A | 2/1997 | Hutchison | |
| 5,611,356 A | 3/1997 | Rothrum | |
| 5,674,189 A | 10/1997 | McDowell et al. | |
| 5,694,643 A | 12/1997 | Fujiwara | |
| 5,707,703 A | 1/1998 | Rothrum et al. | |
| 5,765,566 A | 6/1998 | Rothrum | |
| 5,768,707 A | 6/1998 | Lederer | |
| 5,778,889 A | 7/1998 | Jascomb | |
| 5,778,891 A | 7/1998 | McMahan | |
| 5,784,718 A | 7/1998 | Finnegan | |
| 5,806,094 A | 9/1998 | Kasun et al. | |
| 5,813,051 A | 9/1998 | Counter | |
| 5,813,052 A | 9/1998 | Taylor | |
| 5,816,253 A | 10/1998 | Sosebee | |
| 5,862,525 A | 1/1999 | Tankersley et al. | |
| 5,867,825 A | 2/1999 | Scheerer | |
| 5,916,202 A | 6/1999 | Haswell | |
| 5,973,450 A | 10/1999 | Nishizawa et al. | |
| 5,975,082 A * | 11/1999 | Dowdy | A61B 46/00 128/849 |
| 5,985,395 A | 11/1999 | Comstock et al. | |
| D419,748 S | 2/2000 | Sartori | |
| 6,049,907 A | 4/2000 | Palomo | |
| 6,062,444 A | 5/2000 | Tankersley et al. | |
| 6,105,579 A * | 8/2000 | Levitt | A61B 46/00 128/849 |
| 6,115,840 A | 9/2000 | Hastings | |
| D431,344 S | 10/2000 | Briceno | |
| 6,138,278 A | 10/2000 | Taylor | |
| 6,196,033 B1 | 3/2001 | Dowdle | |
| 6,216,270 B1 | 4/2001 | Moquin et al. | |
| 6,235,659 B1 | 5/2001 | McAmish et al. | |
| 6,244,268 B1 | 6/2001 | Annett | |
| 6,272,685 B1 | 8/2001 | Kumar | |
| 6,285,611 B1 | 9/2001 | Kang | |
| 6,345,622 B1 * | 2/2002 | Chandler | A61B 46/00 128/849 |
| 6,405,730 B2 | 2/2002 | Levitt et al. | |
| 6,378,136 B2 | 8/2002 | Matsushita | |
| D463,093 S | 9/2002 | Murray | |
| 6,449,772 B1 | 9/2002 | Donner et al. | |
| D469,945 S | 2/2003 | Mayer | |
| 6,536,636 B1 | 3/2003 | McDonniel | |
| 6,564,386 B2 | 5/2003 | Fujikawa et al. | |
| 6,601,239 B2 | 8/2003 | Drake | |
| 6,665,880 B2 | 12/2003 | Poppe | |
| 6,694,981 B2 | 2/2004 | Gingles et al. | |
| 6,742,522 B1 | 6/2004 | Baker et al. | |
| 6,820,622 B1 | 11/2004 | Teves et al. | |
| 6,843,252 B2 | 1/2005 | Harrison et al. | |
| 6,990,686 B2 | 1/2006 | Palmer | |
| 7,114,500 B2 | 10/2006 | Bonutti | |
| D533,982 S | 12/2006 | Graneto, III | |
| 7,181,773 B1 | 2/2007 | Piraka | |
| 7,237,271 B1 | 7/2007 | McLandrich | |
| 7,290,547 B2 | 11/2007 | Joseph et al. | |
| 7,293,654 B1 | 11/2007 | Wilson et al. | |
| 7,305,991 B2 | 12/2007 | Santilli et al. | |
| D563,627 S | 3/2008 | Warren | |
| D565,279 S | 4/2008 | Farrell | |
| 7,370,369 B2 | 5/2008 | Cheung | |
| 7,412,728 B2 | 8/2008 | Alesina et al. | |
| D575,936 S | 9/2008 | Fenderson et al. | |
| D579,178 S | 10/2008 | Snyder et al. | |
| 7,454,798 B2 | 11/2008 | Feodoroff | |
| D584,483 S | 1/2009 | Glynn | |
| 7,549,179 B1 | 6/2009 | Saied | |
| D598,638 S | 8/2009 | Graneto, III | |
| 7,594,279 B2 | 9/2009 | Roy | |
| D608,980 S | 2/2010 | Brady | |
| 7,654,266 B2 | 2/2010 | Corbitt, Jr. | |
| D612,126 S | 3/2010 | Milgrom | |
| 7,673,754 B2 | 3/2010 | Wilson, Jr. et al. | |
| D618,884 S | 7/2010 | Zhu | |
| D622,479 S | 8/2010 | Herzog | |
| D622,934 S | 9/2010 | Graneto, III | |
| 7,819,911 B2 | 10/2010 | Anderson et al. | |
| 7,841,020 B2 | 11/2010 | Mayfield et al. | |
| 7,926,120 B2 | 4/2011 | Birmingham | |
| 7,971,274 B2 | 7/2011 | Graneto, III | |
| 8,006,836 B2 | 8/2011 | Trombetta | |
| D646,463 S | 10/2011 | Petrovskis et al. | |
| D647,688 S | 11/2011 | Hilgart | |
| 8,056,146 B2 | 11/2011 | Porowski | |
| 8,069,495 B2 | 12/2011 | Kemper | |
| D653,019 S | 1/2012 | Bond | |
| D655,479 S | 3/2012 | Umbach et al. | |
| D657,530 S | 4/2012 | Farris et al. | |
| 8,162,137 B2 | 4/2012 | Vellutato, Jr. et al. | |
| 8,286,263 B2 | 10/2012 | Sampson-Howlett | |
| 8,332,965 B1 | 12/2012 | Ryer | |
| 8,343,182 B2 | 1/2013 | Kirkham | |
| 8,375,466 B2 | 2/2013 | Tasezen et al. | |
| D680,709 S | 4/2013 | Blood | |
| 8,464,374 B1 | 6/2013 | Thayer | |
| D687,209 S | 8/2013 | Levine | |
| D690,078 S | 9/2013 | Anderson | |
| D698,529 S | 2/2014 | Vanneste | |
| 8,677,513 B2 | 3/2014 | Mathis et al. | |
| D719,721 S | 12/2014 | Bonfiglio | |
| D721,870 S | 2/2015 | Levine | |
| D736,493 S | 8/2015 | Pasko | |
| D737,546 S | 9/2015 | Sewall | |
| D741,044 S | 10/2015 | Pasko | |
| 9,330,799 B1 | 5/2016 | Phillips | |
| D779,155 S | 2/2017 | Pasko et al. | |
| D779,156 S | 2/2017 | Pasko | |
| D785,284 S | 5/2017 | Pasko | |
| D787,780 S | 5/2017 | Pasko | |
| 2001/0032346 A1 | 10/2001 | Matsushita et al. | |
| 2002/0095709 A1 | 7/2002 | Fujikawa et al. | |
| 2003/0060831 A1 | 3/2003 | Bonutti | |
| 2003/0121522 A1 | 7/2003 | Gingles et al. | |
| 2003/0131401 A1 | 7/2003 | Dilworth | |
| 2003/0188753 A1 * | 10/2003 | Jascomb | A61B 46/00 128/853 |
| 2004/0019951 A1 | 2/2004 | Cioffi | |
| 2004/0103904 A1 | 6/2004 | Auerbach et al. | |
| 2004/0123366 A1 | 7/2004 | Schorr et al. | |
| 2004/0172734 A1 | 9/2004 | Hartbrodt | |
| 2005/0044608 A1 | 3/2005 | Ambrose et al. | |
| 2005/0132465 A1 | 6/2005 | Kathumbi-Jackson et al. | |
| 2005/0145254 A1 | 7/2005 | Aboul-Hosn et al. | |
| 2005/0223468 A1 | 10/2005 | Hatton | |
| 2005/0279366 A1 | 12/2005 | Adragna | |
| 2006/0000002 A1 | 1/2006 | Bergkvist | |
| 2006/0064797 A1 | 3/2006 | Pyeatt Rowe | |
| 2006/0081261 A1 | 4/2006 | Corbitt, Jr. | |
| 2006/0107434 A1 | 5/2006 | Rowe | |
| 2006/0117452 A1 | 6/2006 | Ambrose | |
| 2006/0117456 A1 | 6/2006 | Griesbach | |
| 2006/0177655 A1 | 8/2006 | Mizohata et al. | |

(56) References Cited

U.S. PATENT DOCUMENTS

| | | |
|---|---|---|
| 2006/0191541 A1 | 8/2006 | Aboul-Hosn et al. |
| 2006/0236440 A1 | 10/2006 | Zahler |
| 2006/0277655 A1 | 12/2006 | Kerr |
| 2006/0277668 A1 | 12/2006 | Plut et al. |
| 2006/0286334 A1 | 12/2006 | Harpole |
| 2007/0061940 A1 | 3/2007 | Cazares |
| 2007/0102005 A1 | 5/2007 | Bonutti |
| 2007/0113859 A1* | 5/2007 | Allen .......................... A61B 46/00 128/853 |
| 2007/0130668 A1 | 6/2007 | Berman et al. |
| 2008/0006279 A1 | 1/2008 | Bodenham et al. |
| 2008/0023013 A1 | 1/2008 | Tuke et al. |
| 2008/0047567 A1 | 2/2008 | Bonutti |
| 2008/0115253 A1 | 5/2008 | Gorman |
| 2008/0155728 A1 | 7/2008 | Hafer et al. |
| 2008/0178365 A1 | 7/2008 | Furgerson et al. |
| 2009/0165186 A1 | 7/2009 | Mijares et al. |
| 2009/0183529 A1 | 7/2009 | Modiano |
| 2009/0277460 A1 | 11/2009 | Carrez et al. |
| 2009/0320177 A1 | 12/2009 | Lin et al. |
| 2010/0031966 A1 | 2/2010 | Allen |
| 2010/0064408 A1 | 3/2010 | Kemper |
| 2010/0138975 A1 | 6/2010 | Jordan et al. |
| 2010/0186754 A1* | 7/2010 | Carrez .................. A61B 46/00 128/853 |
| 2010/0212063 A1 | 8/2010 | Baucom et al. |
| 2010/0299805 A1 | 12/2010 | Graneto, III |
| 2010/0300459 A1 | 12/2010 | Lair |
| 2010/0313323 A1 | 12/2010 | Tennelle |
| 2011/0023210 A1 | 2/2011 | Porowski |
| 2011/0024485 A1 | 2/2011 | Porowski |
| 2011/0154554 A1 | 6/2011 | Furlong |
| 2011/0167534 A1 | 7/2011 | Wong et al. |
| 2011/0231981 A1 | 9/2011 | Appel et al. |
| 2011/0315150 A1 | 12/2011 | Bream, Jr. |
| 2012/0047623 A1 | 3/2012 | van Oudenallen et al. |
| 2012/0054940 A1 | 3/2012 | Halseth |
| 2012/0060257 A1 | 3/2012 | Herzog |
| 2012/0124722 A1 | 5/2012 | Yadav et al. |
| 2012/0167896 A1 | 7/2012 | Hartmann et al. |
| 2012/0305541 A1 | 12/2012 | Giles |
| 2012/0312308 A1 | 12/2012 | Allen |
| 2013/0091615 A1 | 4/2013 | Pasko et al. |
| 2013/0091616 A1 | 4/2013 | Muche et al. |
| 2013/0191960 A1 | 8/2013 | Pasko |
| 2013/0198930 A1 | 8/2013 | Levine |
| 2013/0239290 A1 | 9/2013 | Rossi |
| 2013/0276204 A1 | 10/2013 | Pasko et al. |
| 2013/0318682 A1 | 12/2013 | Graneto, III |
| 2014/0007316 A1 | 1/2014 | Tommarello et al. |
| 2014/0082816 A1 | 3/2014 | Christopher |
| 2014/0173814 A1 | 6/2014 | Yadav et al. |
| 2014/0182043 A1 | 7/2014 | Moore |
| 2014/0189931 A1 | 7/2014 | Fredrickson |
| 2014/0215681 A1 | 8/2014 | Goodman |
| 2015/0089712 A1 | 4/2015 | Gamble |
| 2015/0096099 A1 | 4/2015 | Vanneste |
| 2015/0113698 A1 | 4/2015 | Gregerson-Brown |
| 2015/0135397 A1 | 5/2015 | Levine |
| 2015/0135398 A1 | 5/2015 | Czajka et al. |
| 2015/0208741 A1 | 7/2015 | Pasko |
| 2015/0213215 A1 | 7/2015 | Kobayashi et al. |

FOREIGN PATENT DOCUMENTS

| | | |
|---|---|---|
| CN | 302083878 | 9/2012 |
| DE | 8904426 | 5/1989 |
| DE | 202006005966 | 10/2006 |
| DE | 102009024999 | 12/2010 |
| DE | 102011016497 | 10/2012 |
| EM | 001320857 | 3/2012 |
| EP | 143204 | 6/1985 |
| EP | 0166124 | 1/1986 |
| EP | 0335041 | 10/1989 |
| EP | 335041 | 10/1989 |
| EP | 1362520 | 11/2003 |
| EP | 1407324-0001 | 5/2014 |
| EP | 1407324-0002 | 5/2014 |
| EP | 1407324-0003 | 5/2014 |
| EP | 1407324-0004 | 5/2014 |
| FR | 2709643 | 3/1995 |
| FR | 2896146 | 7/2007 |
| JP | 2001-510704 | 8/2001 |
| JP | 2011/167417 | 9/2011 |
| KR | 101116311 | 3/2012 |
| WO | 8602258 | 4/1986 |
| WO | 99/04721 | 2/1999 |
| WO | 2001/030258 | 5/2001 |
| WO | 2007/083032 | 7/2007 |
| WO | 2008/146138 | 12/2008 |
| WO | 2011/038792 | 4/2011 |
| WO | 201459401 | 10/2014 |

OTHER PUBLICATIONS

3M Product Clinical Data Summary for No. 1521, 3M Plastic Medical Tape, Jan. 1996 (2 pages).
3M Technical Information Sheet, Product No. 1521, Feb. 2007 (2 pages).
Blue Medical Gown; Manufactured by Medline Industries, Inc.; Unknown availability date but believed to be prior to 1999.
Country Living down under. <URL: http://countrylivingdownunder.yuku.com/topic/6395/How-to-attach-elastic-to-gather-andto-shit#.WQCbi_krJaQ.> Jun. 2, 2014. Gathering with elastic.
Definition of Progressive. Merriam-Webster. Merriam-Webster, n.d. Web. May 17, 2016.
Description and Photographs of 75-1040 Fenestrated Snap Drape (as of Oct. 6, 2008) (1 page).
Description and Photographs of a Perforated Drape With Tear Line (as of Oct. 6, 2008) (1 page).
Description and Photographs of D-09875-001 Snap Drape (as of Oct. 6, 2008) (1 page).
Description and Photographs of Perforated Drapes (as of Oct. 6, 2008) (2 pages).
Disposable Medical Gown; Elastic Cuffs; Salamint, posted at salaaming.com, posting date n/a, copyright 2015 salamin.com, online, site visit Mar. 11, 2016; Available from https://www.salamint.com/productdetail.aspx?id=358.
Disposable Medical Gown; Thumb Loop Plastic Disposable Medical Surgical Gown, posting date n/a, copyright 1999-2016 alibaba.com; site visited Mar. 11, 2016, available from http://www.alibaba.com/product-detail/CPE-Gown-Thumb-loop-White-color_60043196775.html.
European Search Report for European Applicafion No. 09167307.9 dated Oct. 11, 2010 (5 pages).
Fashion Flats, <URLL http:fashion-flats.com/images/1_details_set_in_sleeves.jpr> Visited by Examiner May 21, 2015; Types of set-in sleeves.
Go Japan Go. <URL: http://www.gojapangp.com/fashion/hadajuban_kimono.html>. Visited Feb. 4, 2016. Hadajuban.
Jendela Sastra. <URL: http://www.jendelasatra.com/karya/puisi/hadajuban-dalam-kimono>. Poem with picture published Jan. 10, 2014. Hadajuban (first layer of kimono).
Lyst. <URL: https://ww.lyst.com/clothing/chritophe-lemaire-yak-hair-wool-thumbhole-sweater-moss-stone/.> Visited Apr. 26, 2017 by Examiner of U.S. Appl. No. 29/545,806; Chritophe Lemaire Thumbhole Sweater.
Medical Single Coated Film Tapes Selection Guide—Polyolefin & Vinyl, Nov. 1996 (3 pages).
Rakuten. <URL: http://global.rakuten.com/en/store/753ya/item/100131328/[2/4/2016%201:51:48%20PM]>. Visited Feb. 4, 2016. Hada-Juban.
Sakura-San. <URL: http://www.sakura-san.de/Juban.htm> Saved Jul. 12, 2013. Juban Furisode and Hada-Juban layers for kimono.
The visual dictionary. <RURL: http://www.infovisual.info/06/049_en.html> Jun. 1, 2013. types of cuffs.

(56) References Cited

OTHER PUBLICATIONS

Vintage Patterns Wikia. <URL: https//vintagepatterns.wikia.com/wiki/Butterikc_5374.> visited Dec. 9, 2015. Butterick 5374—Vintage Sewing Blouse Pattern.
"Appeal Decision", U.S. Appl. No. 13/276,232, filed Oct. 18, 2011; dated May 31, 2016.
"BurdaStyle Women's Size Chart", http://www.burdastyle.com/downloads/SizeChart_Regular_inches.pdf; Publication Date Unknown.
"Extended European Search Report", EP Application No. 12790027.2; PCT/US2012/032122; dated Jan. 5, 2015.
"Final OA", U.S. Appl. No. 14/086,798, filed Nov. 21, 2013; dated Feb. 1, 2016.
"First Office Action", CN Application No. 201280046346.4; filed Sep. 11, 2012; dated Aug. 26, 2015.
"Medline Catalog", 2-Ply Sterile Cotton Stockinette by Alba-Waldensian; Medline Catalog; http://www.medline.com/catalog/catalog.jsp; Unknown Publication date but believed to be prior to present application filing date.
"Medline Catalog", Cotton Stockinette by Alba-Waldensian; Medline Catalog; http://www.medline.com/catalog/catalog.jsp; Unknown Publication date but believed to be prior to present application filing date.
"Medline Catalog", Full BodyDrapes by Halyard Health; Medline Catalog; http://www.medline.com/catalog/catalog.jsp; Unknown Publication date but believed to be prior to present application filing date.
"Medline Catalog", K-C100 Mayo Stand Covers by Halyard Health; Medline Catalog; http://www.medline.com/catalog/catalog.jsp; Unknown Publication date but believed to be prior to present application filing date.
"Medline Catalog", Midline Cath Picc Kits by Medikmark; Medline Catalog; http://www.medline.com/catalog/catalog.jsp; Unknown Publication date but believed to be prior to present application filing date.
"Medline Catalog", PICC Full Body Coverage Pack by Halyard Health; Medline Catalog; http://www.medline.com/catalog/catalog.jsp; Unknown Publication date but believed to be prior to present application filing date.
"Medline Catalog", Single Ply Standard Stockinettes by DeRoyal; Medline Catalog; http://www.medline.com/catalog/catalog.jsp; Unknown Publication date but believed to be prior to present application filing date.
"Medline Catalog", Single-Ply Sterile Stockinettes by Kerma Medical; Medline Catalog; http://www.medline.com/catalog/catalog.jsp; Unknown Publication date but believed to be prior to present application filing date.
"Medline Catalog", Sterile Bias Cute Cuttron Stockinette by Alba-Waldensian; Medline Catalog; http://www.medline.com/catalog/catalog.jsp; Unknown Publication date but believed to be prior to present application filing date.
"Medline Catalog", Stockinette by Derma Sciences; Medline Catalog; http://www.medline.com/catalog/catalog.jsp; Unknown Publication date but believed to be prior to present application filing date.
"Medline Catalog", Strl Stockinette Cttn 1-Ply by Alba-Waldensian; Medline Catalog; http://www.medline.com/catalog/catalog.jsp; Unknown Publication date but believed to be prior to present application filing date.
"Medline Catalog", TG Stockinettes by Lohmann and Rauscher; Medline Catalog; http://www.medline.com/catalog/catalog.jsp; Unknown Publication date but believed to be prior to present application filing date.
"Medline Catalog", Tube, Luki 864304; Medline Catalog; http://www.medline.com/catalog/catalog.jsp; Unknown Publication date but believed to be prior to present application filing date.
"Notice of Allowance", Japanese App No. 2015-531859; dated Nov. 24, 2016.
"Office Action", Australian Patent Application 2012304800; dated Nov. 22, 2016.
"Office Action", Canadian Office Action for Canadian Patent No. 2,674,951 dated May 4, 2011 (3 pages).
"Office ACtion", Chinese App No. 201280046346.4; dated Apr. 21, 2016.
"Office Action", Chinese App No. 201280046346.4; dated Oct. 21, 2016.
"Office Action", JP Application No. 2014-531859; dated May 2, 2016.
"Publication", Fashion Flats by Garment Element; by Art Design Projects Inc.; www.fashioncroquis.com; visited May 21, 2015; types of raglan sleeves.
Byun, Sung C., "PCT Search Report", PCT No. PCT/US2012/052079; Filed Aug. 23, 2012; dated Dec. 26, 2012.
Chang, Bong Ho, "PCT Search Report and Written Opinion", PCT/US2012/054659; Filed Sep. 11, 2012; dated Feb. 26, 2013.
Cline, Sally, "Restriction Req", U.S. Appl. No. 13/804,565, filed Mar. 14, 2013; dated Aug. 13, 2015.
Fitts, Carissa, "Final OA", U.S. Appl. No. 29/404,295, filed Oct. 18, 2011; dated Feb. 19, 2015.
Fitts, Carissa, "Final OA", U.S. Appl. No. 29/404,296, filed Oct. 18, 2011; dated Jul. 2, 2015.
Fitts, Carissa, "Final OA", U.S. Appl. No. 29/467,622, filed Sep. 20, 2013; dated Jul. 12, 2016.
Fitts, Carissa, "Final OA", U.S. Appl. No. 29/536,646, filed Aug. 18, 2015; dated Oct. 4, 2017.
Fitts, Carissa, "NonFinal OA", U.S. Appl. No. 29/404,295, filed Oct. 18, 2011; dated Jul. 1, 2014.
Fitts, Carissa, "NonFinal OA", U.S. Appl. No. 29/404,296, filed Oct. 18, 2011; dated Apr. 22, 2016.
Fitts, Carissa, "NonFinal OA", U.S. Appl. No. 29/404,296, filed Oct. 8, 2011; dated Oct. 9, 2014.
Fitts, Carissa, "NonFinal OA", U.S. Appl. No. 29/467,622, filed Sep. 20, 2013; dated Dec. 30, 2015.
Fitts, Carissa, "NonFinal OA", U.S. Appl. No. 29/467,622, filed Sep. 20, 2013; dated May 2, 2017.
Fitts, Carissa, "NonFinal OA", U.S. Appl. No. 29/467,623, filed Sep. 20, 2013; dated Jan. 13, 2016.
Fitts, Carissa, "NonFinal OA", U.S. Appl. No. 29/536,646, filed Aug. 18, 2015; dated Jun. 27, 2017.
Fitts, Carissa, "Notice of Allowance", U.S. Appl. No. 29/404,296, filed Oct. 18, 2011; dated Oct. 7, 2016.
Fitts, Carissa, "Notice of Allowance", U.S. Appl. No. 29/467,622, filed Sep. 20, 2013; dated Sep. 26, 2017.
Fitts, Carissa C, "Notice of Allowance", U.S. Appl. No. 29/467,623, filed Sep. 20, 2013; dated Jan. 13, 2017.
Gimenez Burgos, R, "Extended European Search Report", App No. 12834067.6-1659/2747697; Reference No. SJG/P131778EP00.
Gimenez Burgos, R, "Extended European Search Report", EP 12829356.0-1659/2747696; PCT/US2012052079; Reference No. SJG/P131402EP00; dated Feb. 16, 2015.
Haden, Sally, "Appeal Decision", U.S. Appl. No. 13/925,617, filed Jun. 24, 2013; mailed Jun. 6, 2017.
Haden, Sally, "Final OA", U.S. Appl. No. 13/925,598, filed Jun. 24, 2013; dated Sep. 6, 2016.
Haden, Sally, "NonFinal OA", U.S. Appl. No. 13/276,232, filed Oct. 18, 2011; dated Aug. 11, 2016.
Haden, Sally, "NonFinal OA", U.S. Appl. No. 13/925,532, filed Jun. 24, 2013; dated Jan. 8, 2016.
Haden, Sally, "NonFinal OA", U.S. Appl. No. 13/925,598, filed Jun. 24, 2013; dated Dec. 15, 2015.
Haden, Sally, "NonFinal Office Action", U.S. Appl. No. 13/925,617, filed Jun. 24, 2013; dated May 21, 2018.
Haden, Sally, "Notice of Allowance", U.S. Appl. No. 13/925,617, filed Jun. 24, 2013; dated Sep. 12, 2017.
Haden, Sally C., "Final OA", U.S. Appl. No. 13/276,232, filed Oct. 18, 2011; dated Jul. 17, 2013.
Haden, Sally C., "Final OA", U.S. Appl. No. 13/804,565, filed Mar. 14, 2013; dated May 19, 2016.
Haden, Sally C., "Final OA", U.S. Appl. No. 13/804,565, filed Mar. 14, 2013; dated May 8, 2017.
Haden, Sally C., "Final OA", U.S. Appl. No. 13/925,617, filed Jun. 24, 2007; dated Dec. 3, 2013.
Haden, Sally C., "Final OA", U.S. Appl. No. 13/925,617, filed Jun. 24, 2013; dated Dec. 3, 2013.

(56) References Cited

OTHER PUBLICATIONS

Haden, Sally C., "Final OA", U.S. Appl. No. 14/942,755, filed Nov. 16, 2015; dated Mar. 27, 2018.
Haden, Sally C., "Final Office Action", U.S. Appl. No. 13/276,232, filed Oct. 18, 2011; dated Jan. 13, 2017.
Haden, Sally C., "NonFinal OA", U.S. Appl. No. 13/276,232, filed Oct. 18, 2011; dated Apr. 8, 2013.
Haden, Sally C., "NonFinal OA", U.S. Appl. No. 13/804,565, filed Mar. 14, 2013; dated Oct. 29, 2015.
Haden, Sally C., "NonFinal OA", U.S. Appl. No. 13/925,617, filed Jun. 24, 2013; dated Aug. 13, 2014.
Haden, Sally C., "NonFinal OA", U.S. Appl. No. 13/925,617, filed Jun. 24, 2013; dated Aug. 14, 2013.
Haden, Sally C., "NonFinal OA", U.S. Appl. No. 14/679,628, filed Apr. 6, 2015; dated Sep. 5, 2017.
Haden, Sally Cline, "Final OA", U.S. Appl. No. 13/925,532, filed Jun. 24, 2013; dated Sep. 26, 2016.
Haden, Sally Cline, "NonFinal OA", U.S. Appl. No. 13/804,565, filed Mar. 14, 2013; dated Jan. 19, 2017.
Haden, Sally Cline, "NonFinal OA", U.S. Appl. No. 13/925,532, filed Jun. 24, 2013; dated Aug. 9, 2017.
Haden, Sally Cline, "NonFinal OA", U.S. Appl. No. 13/925,532, filed Jun. 24, 2013; dated May 23, 2016.
Haden, Sally Cline, "NonFinal OA", U.S. Appl. No. 13/925,598, filed Jun. 24, 2013; dated May 24, 2016.
Haden, Sally Cline, "NonFinal OA", U.S. Appl. No. 14/942,755, filed Nov. 16, 2015; dated Sep. 8, 2017.
Haines, Kimberly, "Notice of Allowance", U.S. Appl. No. 13/116,473, filed May 26, 2011; dated May 2, 2017.
Harris, Raymond E., "NonFinal OA", U.S. Appl. No. 12/537,961, filed Aug. 17, 2009; dated Jul. 17, 2012.
Harris, Raymond E., "Final OA", U.S. Appl. No. 12/537,961, filed Aug. 7, 2009; dated Nov. 21, 2012.
Harris, Raymond E., "Final Office Action", U.S. Appl. No. 12/537,961, filed Aug. 7, 2009; dated Apr. 11, 2012.
Harris, Raymond E., "Non-Final Office Action", U.S. Appl. No. 12/537,961, filed Aug. 7, 2009; dated Nov. 9 2011.
Hicks, Victoria, "Final OA", U.S. Appl. No. 13/116,473, filed May 26, 2011; dated Nov. 22, 2013.
Hicks, Victoria, "Final OA", U.S. Appl. No. 13/229,743, filed Sep. 11, 2011; dated Aug. 7, 2014.
Hicks, Victoria, "Final OA", U.S. Appl. No. 13/589,640, filed Aug. 20, 2012; dated Jan. 2, 2015.
Hicks, Victoria, "NonFinal OA", U.S. Appl. No. 13/116,473, filed May 26, 2011; dated May 16, 2013.
Hicks, Victoria, "NonFinal OA", U.S. Appl. No. 13/229,743, filed Sep. 11, 2011; dated Feb. 10, 2014.
Hicks, Victoria, "NonFinal OA", U.S. Appl. No. 13/589,640, filed Aug. 20, 2012; dated Jun. 13, 2014.
Hicks, Victoria, "Notice of Allowance", U.S. Appl. No. 13/116,473, filed May 26, 2011; dated Aug. 15, 2017.
Hicks, Victoria, "Notice of Allowance", U.S. Appl. No. 13/229,743, filed Sep. 11, 2011; dated Jan. 2, 2018.
Hicks, Victoria, "Notice of Allowance", U.S. Appl. No. 13/589,640, filed Aug. 20, 2012; dated Dec. 19, 2017.
Lee, Cheol Soo, "International Search Report", PCT/US2012/032122; Filed Apr. 4, 2012; dated Nov. 1, 2012.
Lee, Jong Kyung, "PCT Search Report and Written Opinion", PCT/US2014/023432; Filed Mar. 11, 2014; dated Jul. 10, 2014.
McVey, Lauren, "Ex Parte Quayle", U.S. Appl. No. 29/467,603, filed Sep. 20, 2013; Mailed Jul. 26, 2017.
McVey, Lauren, "Final OA", U.S. Appl. No. 29/459,047, filed Jun. 25, 2013; dated Sep. 24, 2015.
McVey, Lauren, "Final OA", U.S. Appl. No. 29/467,616, filed Sep. 20, 2013; dated Nov. 3, 2015.
McVey, Lauren, "Final OA", U.S. Appl. No. 29/467,619, filed Sep. 20, 2013; dated Oct. 20, 2015.
McVey, Lauren, "Final OA", U.S. Appl. No. 29/467,621, filed Sep. 20, 2013; dated Apr. 11, 2016.
McVey, Lauren, "Final OA", U.S. Appl. No. 29/467,603, filed Sep. 20, 2013; dated Feb. 10, 2016.
McVey, Lauren, "Final Office Action", U.S. Appl. No. 29/467,603, filed Sep. 20, 2013; dated Feb. 8, 2017.
McVey, Lauren, "Final Office Action", U.S. Appl. No. 29/545,802, filed Nov. 16, 2015; dated May 17, 2018.
McVey, Lauren, "NonFinal OA", U.S. Appl. No. 29/459,047, filed Jun. 25, 2013; dated Apr. 23, 2015.
McVey, Lauren, "NonFinal OA", U.S. Appl. No. 29/467,603, filed Sep. 30, 2015; dated Jun. 30, 2015.
McVey, Lauren, "NonFinal OA", U.S. Appl. No. 29/467,612, filed Sep. 20, 2013; dated Jun. 5, 2015.
McVey, Lauren, "NonFinal OA", U.S. Appl. No. 29/467,616, filed Sep. 20, 2013; dated Jun. 17, 2015.
McVey, Lauren, "NonFinal OA", U.S. Appl. No. 29/467,621, filed Sep. 20, 2013; dated Aug. 26, 2015.
McVey, Lauren, "NonFinal OA", U.S. Appl. No. 29/467,625, filed Sep. 20, 2013; dated Jul. 29, 2015.
McVey, Lauren, "NonFinal OA", U.S. Appl. No. 29/545,802, filed Nov. 16, 2015; dated Jun. 1, 2017.
McVey, Lauren, "NonFinal OA", U.S. Appl. No. 29/545,805, filed Nov. 16, 2015; dated Jun. 2, 2017.
McVey, Lauren, "NonFinal OA", U.S. Appl. No. 29/545,806, filed Nov. 16, 2015; dated Jun. 1, 2017.
McVey, Lauren, "Notice of Allowance", U.S. Appl. No. 29/459,047, filed Jun. 25, 2013; dated Aug. 10, 2016.
McVey, Lauren, "Notice of Allowance", U.S. Appl. No. 29/459,047, filed Jun. 25, 2013; dated Oct. 19, 2016.
McVey, Lauren, "Notice of Allowance", U.S. Appl. No. 29/459,060, filed Jun. 25, 2013; dated Apr. 23, 2015.
McVey, Lauren, "Notice of Allowance", U.S. Appl. No. 29/467,616, filed Sep. 20, 2013; dated Aug. 10, 2016.
McVey, Lauren, "Notice of Allowance", U.S. Appl. No. 29/467,620, filed Sep. 20, 2013; dated Jun. 23, 2015.
McVey, Lauren, "Notice of Allowance", U.S. Appl. No. 29/467,621, filed Sep. 20, 2013; dated Oct. 20, 2016.
McVey, Lauren, "Notice of Allowance", U.S. Appl. No. 29/467,623, filed Sep. 20, 2013; dated Aug. 30, 2016.
McVey, Lauren D., "NonFinal OA", U.S. Appl. No. 29/467,619, filed Sep. 20, 2013; dated May 20, 2015.
Oprea, Karen, "NonFinal OA", Canadian Application No. 2,847,495; dated Jan. 22, 2018.
Oprea, Karen, "NonFinal OA", Canadian Application No. 2,848,634; dated Mar. 15, 2018; Reference No. 15468-P45942CA00.
Pandika, Kylie, "Examination Report", Australian Patent Application No. 2012312845; Filed Sep. 23, 2011; dated Nov. 1, 2016.
Reed, Richard, "First Examination Report", Australian Application No. 2012259325; Exam Request Date Mar. 5, 2015; Reference No. 35210639/GCP; dated Nov. 30, 2015.
Sato, Tomoya, "NonFinal Office Action", Japanese Patent Application No. 2017-121386; dated Dec. 27, 2017.
Vanatta, Amy, "Non-Final Office Action", U.S. Appl. No. 12/720,360, filed Mar. 9, 2010; dated Oct. 11, 2011.
Vanatta, Amy B., "Notice of Allowance", U.S. Appl. No. 12/720,360, filed Mar. 9, 2012; dated Feb. 9, 2012.
Walshon, Rashida, "Final OA", U.S. Appl. No. 29/506,290, filed Oct. 14, 2014; dated Jul. 28, 2016.
Walshon, Rashida, "NonFinal OA", U.S. Appl. No. 29/506,290, filed Oct. 14, 2014; dated Jan. 20, 2016.
Walshon, Rashida, "NonFinal OA", U.S. Appl. No. 29/591,354, filed Jan. 19, 2017; dated Oct. 4, 2017.
Walshon, Rashida, "Non-Final OA", U.S. Appl. No. 29/591,354, filed Jan. 19, 2017; dated Apr. 17, 2018.
Wright, Jennifer, "NonFinal OA", U.S. Appl. No. 29/506,294, filed Oct. 14, 2014; dated Mar. 28, 2016.
Wright, Jennifer, "NonFinal OA", U.S. Appl. No. 29/506,294, filed Oct. 14, 2014; dated Sep. 23, 2016.
Wu, Jocelyn Mary, "NonFinal OA", U.S. Appl. No. 14/086,798, filed Nov. 21, 2013; dated Sep. 24, 2015.
Ambrosch, Jeannette, "Notice of Allowance", EP Application No. 12834067.6; dated Oct. 11, 2019.
Bravo, Jocelyn, "NonFinal OA", U.S. Appl. No. 14/086,798, filed Nov. 21, 2013; dated May 20, 2019.

(56) References Cited

OTHER PUBLICATIONS

Bravo, Jocelyn M., "NonFinal OA", U.S. Appl. No. 14/086,798, filed Nov. 21, 2013; dated Dec. 11, 2019.
Emirdag, Eda, "Exam Report", EP Application No. 12829356.0-1113; dated Sep. 12, 2019.
Emirdag, Eda, "Office Action", European Application No. 12829356.0; dated Apr. 8, 2020.

* cited by examiner

ZIP STRIP DRAPING SYSTEM AND METHODS OF MANUFACTURING SAME

CROSS REFERENCE TO PRIOR APPLICATIONS

This application is a divisional application claiming priority and benefit from U.S. application Ser. No. 13/589,640, filed Aug. 20, 2012, which is incorporated herein by reference for all purposes, which is (1) a continuation-in-part of U.S. application Ser. No. 12/188,931, filed Aug. 8, 2009, which is also incorporated by reference for all purposes, and (2) claims priority under 35 USC § 119(e) to U.S. provisional application Ser. No. 61/538,542, which is also incorporated herein by reference for all purposes.

BACKGROUND

Technical Field

This invention relates to medical drapes, and more specifically to a medical drape system having a tearing feature for easy and clean removal of the drape from a patient.

Background Art

Medical drapes are widely used during the performance of surgical and other medical procedures as a protective measure. Medical drapes may be used to cover a patient during surgical or other medical procedures. Medical drapes are made sterile and are intended to prevent the possibility of infection being transmitted to the patient. Medical drapes provide protection to the patient by creating a sterile environment surrounding the surgical site and maintaining an effective barrier that minimizes the passage of microorganisms between non-sterile and sterile areas.

It would be advantageous to have medical drapes configured to reduce contamination of sterile fields during medical procedures.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
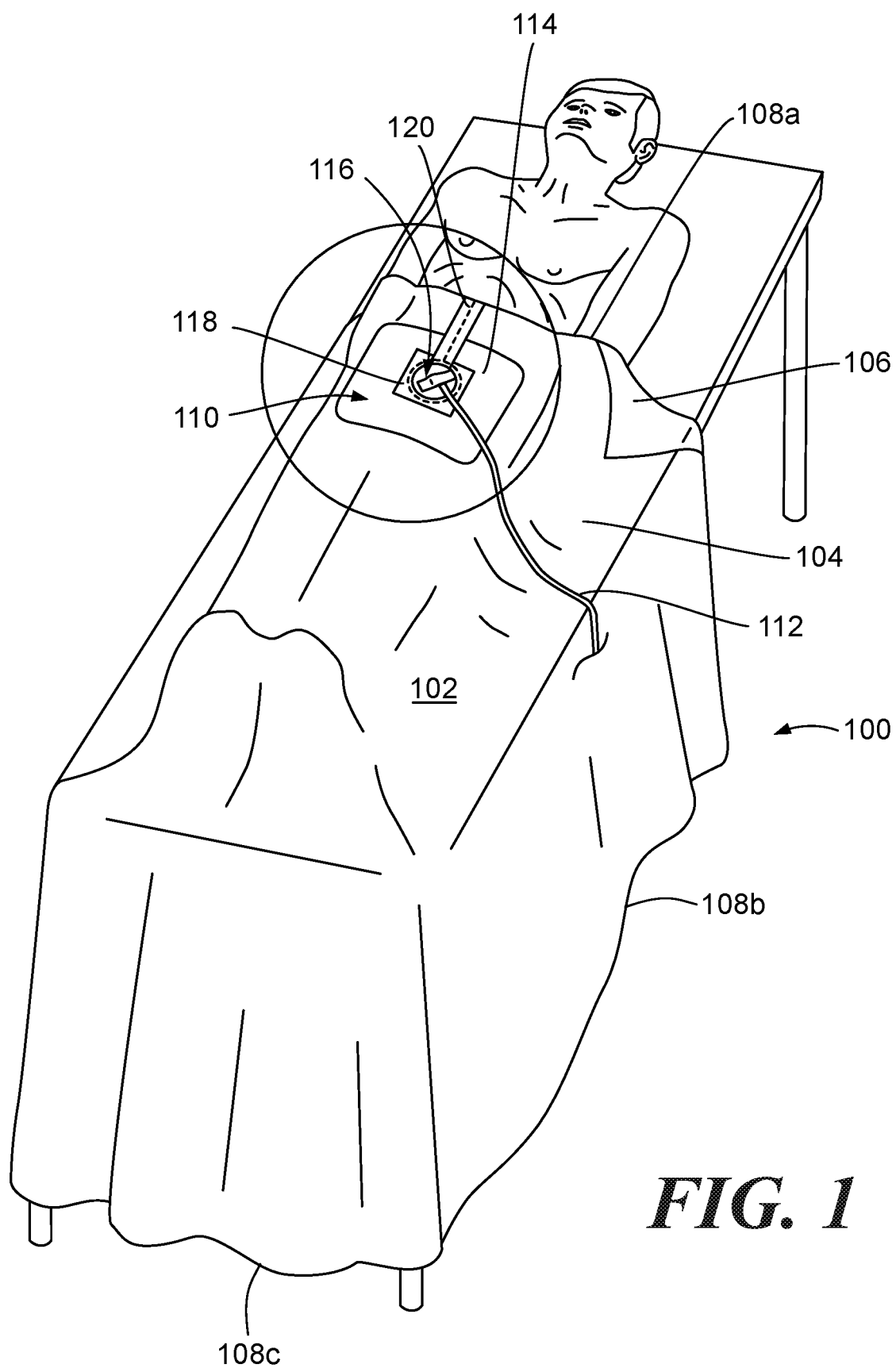
FIG. 1 is a perspective view illustrating a medical drape in a medical procedure, according to one embodiment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Healthcare facilities are increasingly concerned about the occurrence of secondary complications occurring during medical and surgical procedures. For example, during a medical procedure on an otherwise healthy patient, such as the insertion of an intravenous catheter, there is the possibility that a secondary infection or other complication can result. As a result, more attention is being turned to establishment and maintenance of sterile fields about patients and procedure sites during medical procedures. For example, some healthcare facilities request medical professionals to check and double check certain conditions, such as whether a proper sterile field has been established or whether a proper sterile field can be maintained. Despite these warnings, it can some times be difficult to remember to check and double check each condition. Further, it can be difficult to maintain sterile fields with some currently existing equipment.

Medical drapes may, for example, be manufactured for use in connection with catheters such as central venous catheters (CVCs). CVCs may be used, for example, for intravenous drug therapy and/or parenteral nutrition. If the catheter or area surrounding the catheter becomes contaminated during or after being inserted into a patient, complications such as catheter site infection, suppurative phlebitis, and/or septicemia may result.

To minimize the risk of infection associated with catheterization, medical drapes often include fenestrations, or apertures, that extend completely through the drape to provide access to an adjacent area of the patient's body (for example, the subclavian area, the brachial area, or the femoral area) over which the respective fenestration lies. Because of the open nature of the fenestrations, a catheter may be inserted through the fenestrations and into the area of the patient's body adjacent to the fenestrations.

It has been generally problematic to remove the medical drape after the medical or surgical procedure is completed. For example, to remove the medical drape, scissors have been used to cut the medical drape from an exterior edge to a fenestration. The use of scissors near the site of the medical or surgical procedure and near the patient is not only awkward and, often, messy, but it is likely to cause injury to the patient or to the user, and can cause damage by cutting catheter or intravenous (IV) lines.

Some current medical drapes include perforations that pass completely through the drape and that form a weakened line, also referred to as a scoreline. To remove the drape, the user pulls the drape apart by hand without the use of any tools, such as scissors. However, one problem associated with this type of scoreline is that the sterile field is reduced because microorganisms can easily pass through the perforations.

Another problem associated with this type of medical drape is that, in general, the scorelines do not allow an easy or clean tear. For example, the tearing motion may require numerous attempts to initiate and complete the tear; the tearing motion may result in a tear-line that is different than the scoreline; and/or the tearing motion may encounter too much material resistance to complete the tear. A scoreline that does not easily tear can lead to frustration of the user, who is likely to continuously pull on the medical drape with a larger and unnecessary force. This, in turn, can lead to contaminants breaching the sterile field and, possibly, to other injuries or damage. For example, constant pulling on the medical drape can cause expensive medical instruments to fall down, or can cause sharp medical instruments to injure other staff, the patient, or the user. Additionally, the pulling involved with the larger and unnecessary force may cause discomfort to the patient who is the recipient of the larger and unnecessary force.

Other current medical drapes include an adhesive tape strip positioned along the length of a drape cut to overlap two adjacent sides of the drape cut. The adhesive tape strip is securely fixed to one side of the drape cut and is removably attached to the other (adjacent) side of the drape cut.

Similar to the medical drapes having scorelines, this type of medical drape fails to provide an easy and clean tear. The removably attached side of the adhesive tape strip often encounters resistance that interferes with easy removal of the medical drape. Furthermore, inadvertent pulling on the medical drape during or before the medical procedure can cause gaps between the removably attached side of the adhesive tape strip and the side of the drape cut to which it is attached. As such, the potential for contaminating the sterile field is greatly increased. Moreover, this type of medical drape involves additional manufacturing steps and costs, such as including a first layer of a permanent adhesive (on the fixed side of the adhesive tape strip) and a second layer of a removable adhesive (on the removable side of the adhesive tape strip). Thus, it would be desirable to have a medical drape that assists in addressing one or more of the above problems. Embodiments of the present invention do just that.

According to one embodiment, a medical drape has a tool-less removal feature and includes a drape material, a drape cut, an adhesive tape strip, and a scoreline. The drape material has a top side, a back side, and at least one exterior edge. The drape cut has a starting point at the exterior edge and extends completely through the thickness of the drape material. The adhesive tape strip is positioned along the length of the drape cut to overlap at least a portion of the drape material on both sides of the drape cut to initially secure the two adjoining cut edges to each other. The scoreline extends along the length of the adhesive tape strip and only partially through the thickness of the adhesive tape strip to permit easy tearing of the adhesive tape strip for separation of the two adjoining cut edges.

According to another embodiment, a method for manufacturing an easily tearable medical drape includes providing a drape material having a top surface and a back surface, the back surface being positioned in contact with a patient when the medical drape is in use, the drape material having at least one exterior edge. The drape material is completely severed to form a drape cut extending from the exterior edge of the drape material to at least an inner area of the drape material, the drape cut being defined by two adjacent cut edges. The two adjacent cut edges are secured to each other by positioning an adhesive strip overlappingly with the drape cut, the adhesive strip extending over a portion of each of the two adjacent cut edges. The adhesive strip is partially severed through its thickness to form a strip scoreline extending along a length of the adhesive strip, the strip scoreline overlapping the drape cut to permit easy tearing of the adhesive strip for separation of the two adjoining cut edges.

According to yet another embodiment, a method for manufacturing a medical drape includes providing a sheet having at least one layer of drape material, and severing the sheet completely through its thickness from an outer edge of the sheet to an inner area of the sheet to form a sheet cut. The sheet cut separates a first sheet area from an adjacent second sheet area. A strip is provided for securing the first sheet area to the second sheet area. The strip is partially severed through its thickness to form a strip scoreline, the strip scoreline separating a first strip area and an adjacent second strip area. A portion of the first strip area is fixed to a portion of the first sheet area and a portion of the second strip area to a portion of the second sheet area such that the strip scoreline is in an overlapping position with respect to the sheet cut.

The above summary of the present invention is not intended to represent each embodiment or every aspect of the present invention. The detailed description and Figures will describe many of the embodiments and aspects of the present invention.

In surgical procedures, many times intravenous (IV) lines or other delivery or drainage lines must remain in the patient after the procedure is complete. Described below in more detail is a medical system for removing a medical or surgical drape after completing a medical or surgical procedure without dislodging any remaining lines. The medical system includes features directed to manually tearing apart the medical drape, by hand, without using any tools (e.g., scissors). An advantage of the medical system is that it eliminates the potential for injury or damage caused by the tools. Another advantage of the medical system is that it consistently provides a clean and smooth tear in the medical drape. A further advantage of the medical system is that the tearing can be easily accomplished with the exertion of little force. Yet another advantage of the medical system is that it eliminates the potential for contamination of a sterile field, by adequately sealing adjoining edges of a drape cut in the medical drape.

Referring to FIG. 1, a medical drape 100 according to one embodiment of the medical system is illustrated generally as it would appear after being unfolded and ready for use in a surgical or medical procedure (for example, catheterization, angiography, and radiology). The medical drape 100 is generally a single use disposable drape and includes a main drape material 102 and has dimensions suitable for covering the patient's entire body, including, in some embodiments, the patient's head and face to assist in maintaining the sterility of the surgical area and thereby lower the risk of infection. In such embodiments, the total length of the medical drape 100 generally ranges from about 115 in. to about 125 in. (about 292 cm to about 318 cm). In other embodiments, the medical drape 100 may cover less than the patient's entire body and may have a length ranging generally from about 24 in. to about 150 in. (about 61 cm to about 381 cm). The total width of the medical drape 100 generally ranges from about 24 in. to about 80 in. (about 61 cm to about 204 cm).

The medical drape 100 has a front side 104, which faces away from a patient when in use, and a back side 106, which contacts the patient when in use. The medical drape 100 includes a plurality of exterior edges 108a-108c. The main drape material 102 is generally made of a water-repellent or water-impermeable material and/or is coated with such a water-repellent or water impermeable material to prevent the passage of bodily fluids and/or contaminating microorganisms. For example, the main drape material 102 can include various woven, non-woven, hydroentangled materials, and/or combinations thereof. The base fabrics used in the main drape material 102 may include absorbent Airlaid, spunlace, blends of polyester, polypropylene, polyethylene, urethane, and/or combinations thereof. The drape material 102 may be manufactured using various methods, including a spunbond metblown spundbond (SMS) method, a spunbond metblown metblown spundbond method (SMMS), and a spunbond metblown metblown spundbond method (SMMMS).

A fenestration 110 is optionally positioned on and extends completely through the thickness of the main drape material 102. The fenestration 110 allows for a surgical or other medical procedures to be performed therethrough. For example, a catheter tube 112 can be attached directly to the patient through the fenestration 110. In alternative embodiments, additional fenestrations can be positioned on the main drape material 102 and in any suitable location on the main drape material 102. Furthermore, although the fenestration 110 has been illustrated to be generally rectangular in the described embodiment, in alternative embodiments the fenestration(s) can be generally circular, egg-shaped, oval-shaped, pear-shaped, football-shaped, or the like. It is further contemplated that the drape may have any of the properties described herein, regardless of the shape, number, and/or location of the fenestrations.

The fenestration 110 may be covered at least in part with an incise film 114. The composition of the incise film 114 is well known to those skilled in the art of medical drapes. One example of an incise film that may be used is OpSite® Incise film manufactured by Smith & Nephew, Inc. (Memphis, Tenn.). The incise film 114 may be generally transparent so that the health care provider may have clear visibility for locating the correct position for inserting the catheter tube 112 or otherwise accessing the patient site. The incise film 114 may be positioned on the front side 104 or on the back side 106 of the medical drape 100, so long as an exposed adhesive side of the incise film 114 faces toward the patient. The incise film 114 is intended to be removably fixed to the patient, e.g., by attaching the adhesive side to the patient, during the procedure. As such, removal of the medical drape 100 from the patient may be difficult to accomplish without exerting tugging and/or pulling on the medical drape 100 (and, consequently, on the patient), unless removal features are included in the medical drape 100 to facilitate easy tearing.

The incise film 114 includes, optionally, an access port 116 being positioned on and extending completely through the incise film 114. The access port 116 allows the catheter tube 112 to be readily inserted without any cutting, puncturing, or further modification of the medical drape 100 or incise film 114. Although the access port 116 of the illustrated embodiment is circular, it is contemplated that other general shapes including, but not limited to, rectangles, other polygons, circles, and ovals may be used. The access port 116 may have an area ranging from about 3 in2 to about 5 in2 (about 19 cm2 to about 33 cm2). Optionally, additional access ports can be included.

The exposed adhesive side of the incise film 114 is generally covered by at least one release liner 118, which is located on the back side 106 of the main drape material 102. Although the release liner 118 is generally removed when the medical drape 100 is placed over the patient, the release liner 118 of FIG. 1 is shown for illustration purposes. The release liner 118 may be one continuous piece of liner, strips, or the like. When the release liner 118 is removed, the adhesive side of the incise film 114 may be coupled to the patient to keep the medical drape 100 and, in particular, the fenestration 110 in place during the procedure.

An adhesive tape strip (or zip strip) 120 is positioned on the main drape material 102, extending from a top exterior edge 108a of the medical drape 100 internally to the access port 116. For example, the adhesive tape strip 120 is glued to the front side 104 of the main drape material 102. Optionally, the adhesive tape strip 120 is glued to the back side 106. In alternative embodiments, the adhesive tape strip 120 extends from any exterior edge 108a-108c to any internal area of the main drape material 102 or to another exterior edge 108a-108c. Any number of adhesive tape strips 120 can be included in the medical drape 100 in any orientation.

According to one embodiment, the adhesive tape strip 120 is a single-coated polyethylene medical tape, such as a medical tape manufactured by 3M (St. Paul, Minn.) as product number 1521. The 3M Medical Tape 1521 is a single-coated tape having a matte finish which includes a transparent polyethylene and is coated with a hypoallergenic, pressure sensitive acrylate adhesive and includes a liner that is silicone treated and is polyethylene coated on one side only along with a bleached Kraft paper release liner. The 3M medical tape has a tape caliper of 6.4 mil (0.16 mm) of polyethylene film tape, a backing of 5.0 mil (0.13 mm) translucent polyethylene film, an acrylate adhesive (designed for medical/surgical use), and a release liner of 83 lb poly-coated Kraft paper, with silicone on one side (6 mils/0.15 mm). The adhesion to steel of the 3M Medical Tape 1521 is 21 ounces/inch width (0.6 kg/25 mm width). Other suitable medical tapes manufactured by 3M and/or other manufacturers may be used in connection with the adhesive tape strip 120.

Figure 2A:
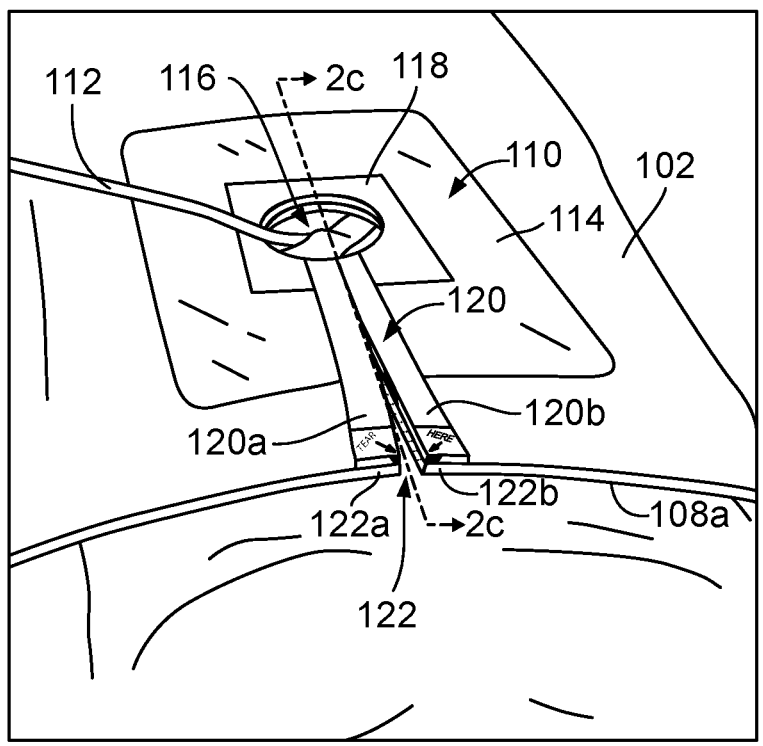
FIG. 2A is an enlarged perspective view illustrating an adhesive tape strip having a scoreline and being attached to the medical drape of FIG. 1.
Figure 2B:
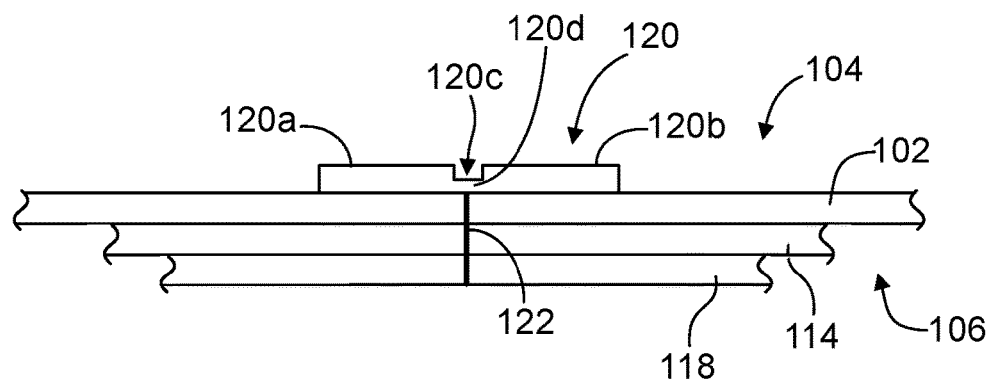
FIG. 2B is, generally, a front view of FIG. 2A illustrating the depth of the scoreline through the thickness of the adhesive tape strip.
Figure 2C:
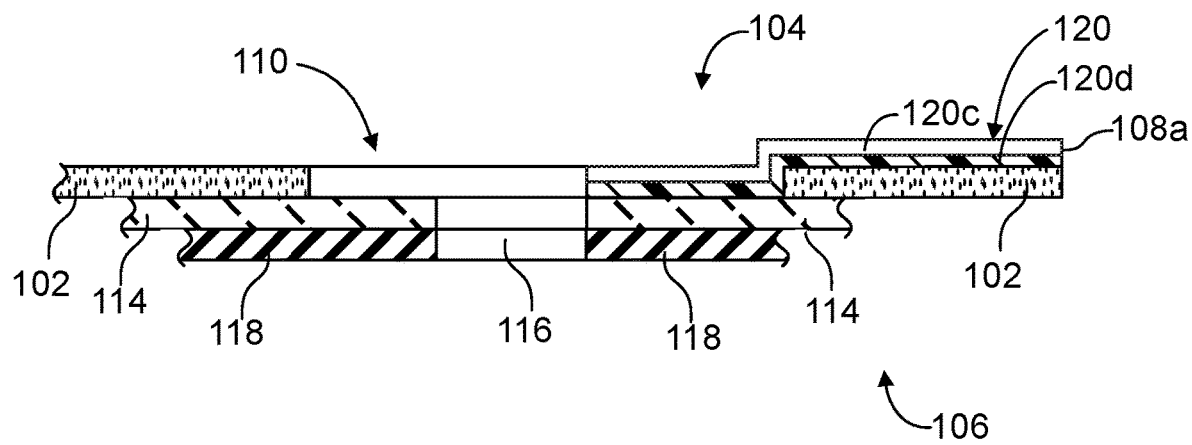
FIG. 2C is, generally, a cross-sectional side view of FIG. 2A illustrating the depth of the scoreline along the length of the adhesive tape strip.

Referring to FIGS. 2A-2C, the adhesive tape strip 120 generally includes a first strip side 120a and a second strip side 120b, which are connected along a strip scoreline 120c via a bridging area 120d. The strip scoreline 120c is generally formed by severing the adhesive tape strip 120 along its length partially through its thickness such that a separated area is formed above the bridging area 120d between the first strip side 120a and the second strip side 120b. Thus, based at least in part on the relatively small thickness of the bridging area 120d, the first strip side 120a can be easily separated from the second strip side 120b. Also, the adhesive tape strip 120 can be easily separated from the main drape material 102 by selecting an appropriate removable adhesive material when fixing the adhesive tape strip 120 to the main drape material 102. In this exemplary embodiment, the strip scoreline 120c is generally centrally positioned along the width (i.e., narrow dimension) of the adhesive tape strip 120.

The adhesive tape strip 120 is positioned such that the strip scoreline 120c overlaps a drape cut 122 of the medical drape 100. The drape cut 122, in one embodiment, is formed by completely severing the main drape material 102, the incise film 114, and the release liner 118, from the top exterior edge 108a through the access port 116. In another embodiment, the drape cut 122 is formed by partially severing the main drape material 102, and either partially or completely severing the incise film 114 and the release liner 118. In yet another embodiment, the drape cut 122 can be formed by perforating the main drape material 120, and one of partially severing, completely severing, or perforating the incise film 114 and the release liner 118 as well. Other methods of forming the drape cut 122 will be obvious to those of ordinary skill in the art having the benefit of this disclosure.

In one embodiment, the drape cut 122 is generally defined by two adjoining cut edges, a first cut edge 122a and a second cut edge 122b. The adhesive tape strip 120 secures the adjoining first and second cut edges 122a, 122b of the drape cut 122 to each other by having the first strip side 120a fixed (e.g., glued) to the a first cut edge 122a and having the second strip side 120b fixed to the second cut edge 122b. The bridging area 120d is the only material that holds together the first and second cut edges 122a, 122b.

In addition to securing the drape cut 122, the adhesive tape strip 120 seals the drape cut 122 to eliminate any violation of a sterile field formed on the patient side. Because the strip scoreline 120c extends only through part of the thickness of the adhesive tape strip 120, a protective barrier—the bridging area 120d—is inherently present during the medical procedure.

Figure 3:
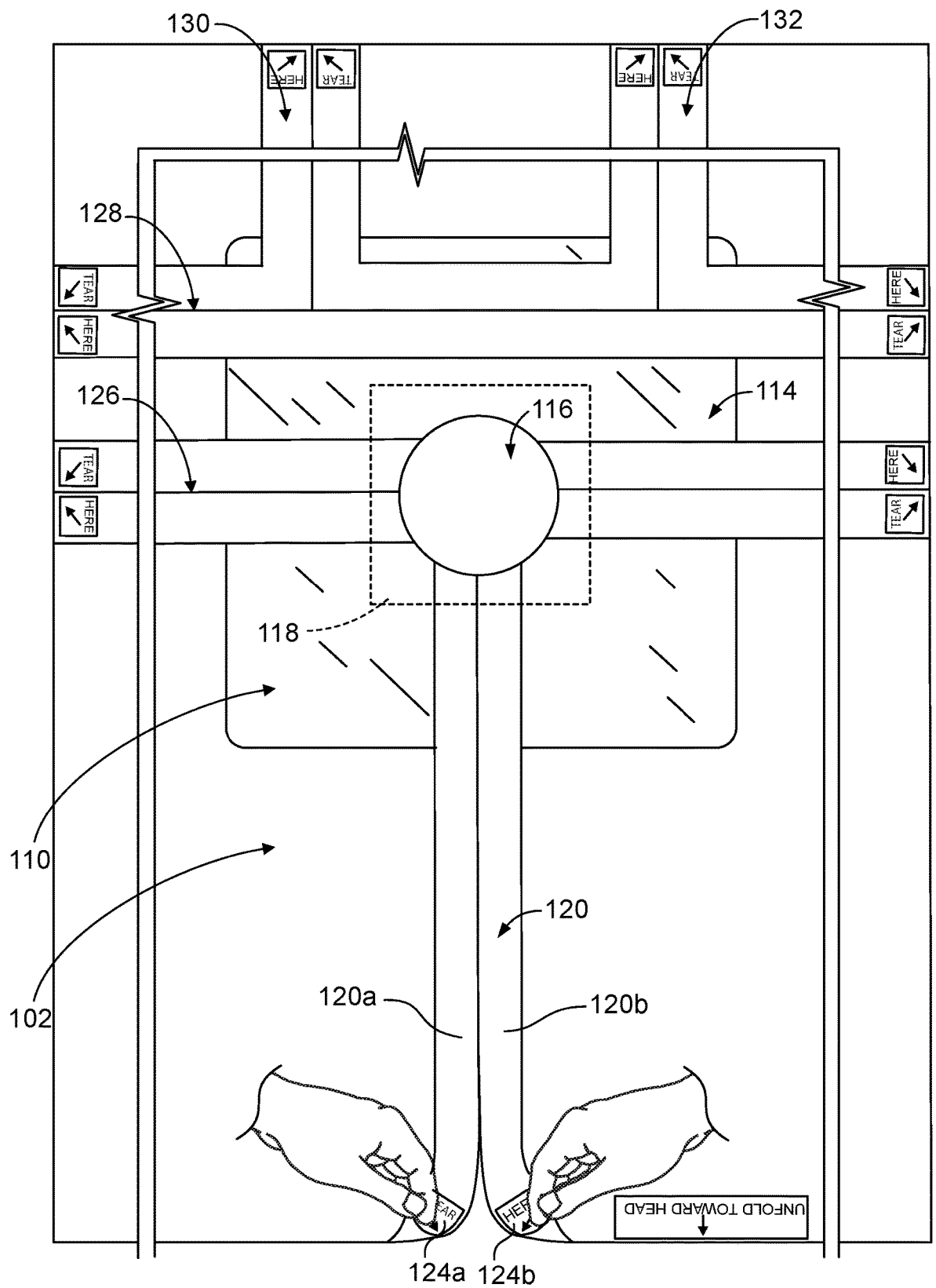
FIG. 3 is a perspective view illustrating the act of tearing of the adhesive tape strip.

Referring to FIG. 3, the medical drape 100 is easily removed after the medical or surgical procedure is completed. A staff person pulls apart two indicators 124a, 124b, which may be generally indicated as "Tear Here," "Rip Here," "Separate Here," "Pull Apart Here," "Pull Here," or "Snap Here," of the medical drape 100 to tear apart the adhesive tape strip 120 along the strip scoreline 120c. The first and second strip sides 120a, 120b are simply pulled apart as the material of the bridging area 120d is being torn. Because, the drape cut 122 is a complete sever of the materials associated with the main drape material 102, the incise film 114, and the release liner 118, these materials provide no resistance to the act of tearing, i.e., they are pre-cut. Consequently, the tearing of the adhesive tape strip 120 provides a smooth and clean tear. As a further advantage, the tearing of the adhesive tape strip 120 can be easily accomplished with the exertion of little force that renders the drape system simple for use from both the user's and the patient's perspective.

Optionally, one or more additional adhesive tape strips 126, 128, 130, 132 can be positioned on the drape material 102. The adhesive tape strips 126, 128, 130, 132 can be positioned and oriented in any location, can extend from any area to any other area of the drape material 102, and can be of any suitable number.

Figure 4:
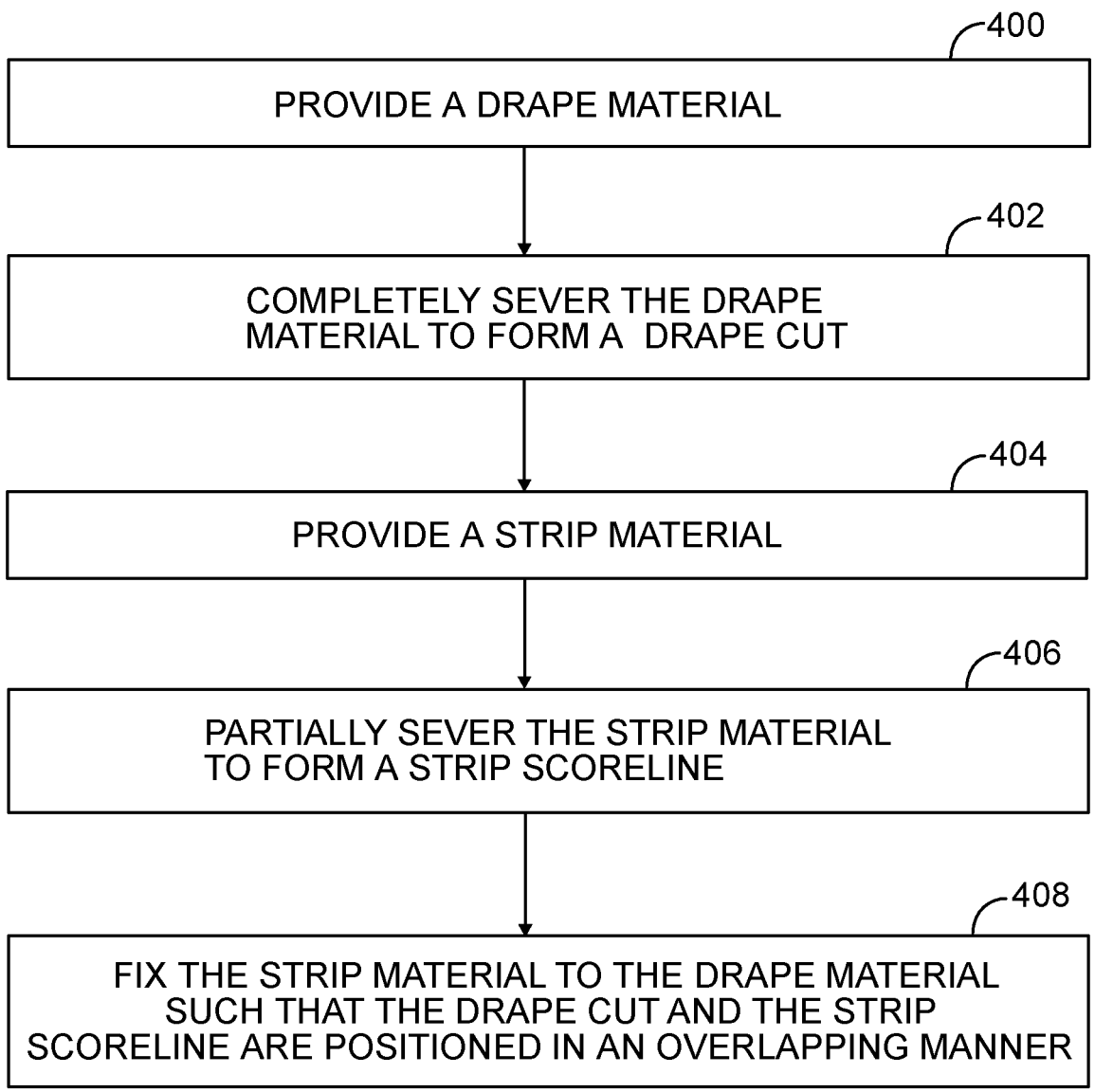
FIG. 4 is a flowchart illustrating a method for making the medical drape of FIG. 1, according to an alternative embodiment.

Referring to FIG. 4, a method of manufacturing the medical drape 100 includes providing a drape material (400) and completely severing the drape material to form a drape cut (402). A strip material is provided (404) and a partial sever of the strip material is made to form a strip scoreline (406). The strip material, for example, can have a thickness of about 0.2 inches (about 5 mm), a width of about 1.5 inches (about 38 mm) to about 3 inches (about 76 mm), and can extend from about 35% to about 60% through the thickness of the strip material (e.g., about 0.07 inches to about 0.12 inches, or about 1.8 mm to about 3 mm). The strip material is fixed to the drape material such that the drape cut and the strip scoreline are positioned in an overlapping manner (408).

Figure 5:
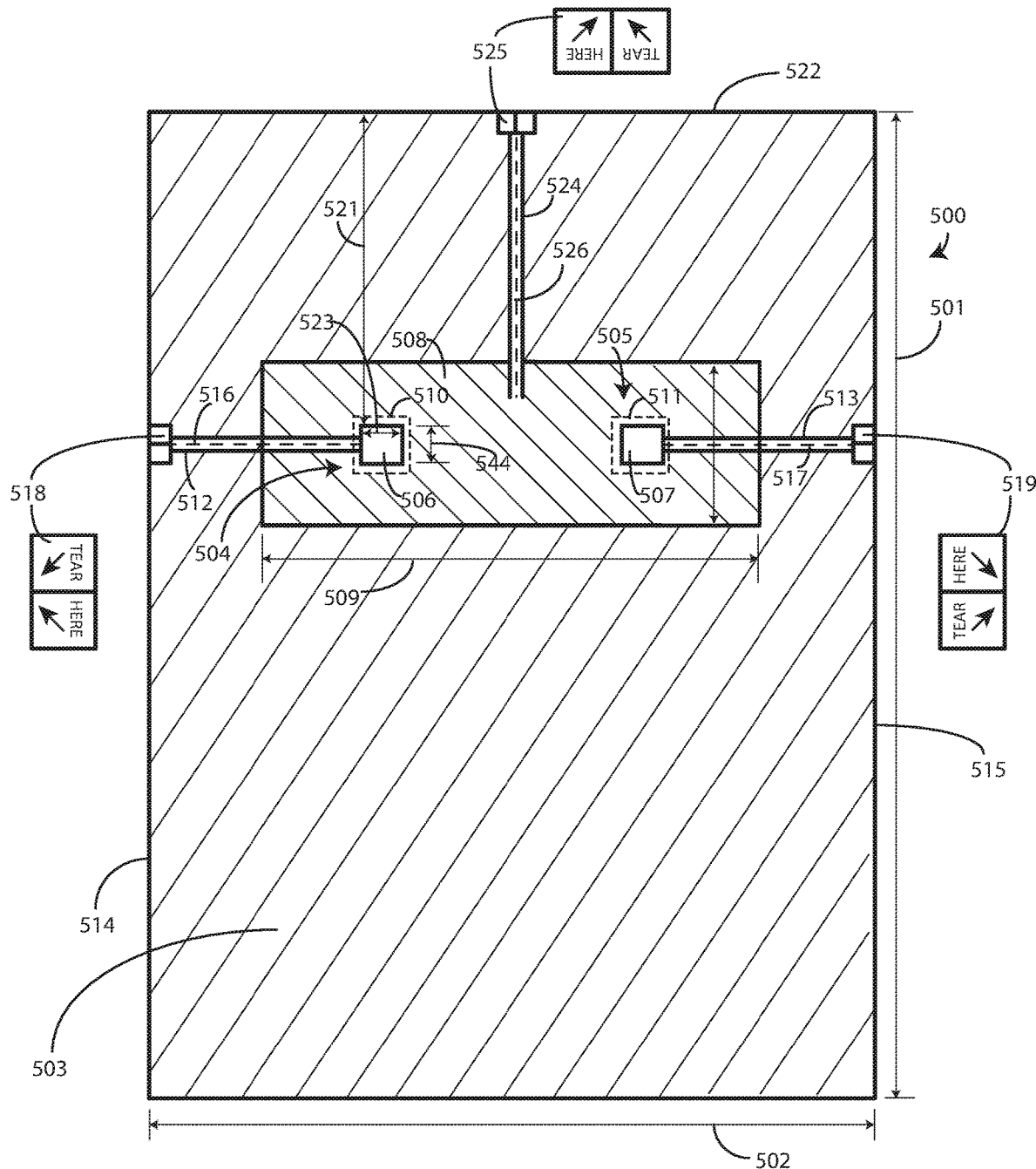
FIG. 5 is a front view of another medical drape according to one embodiment.
Figure 6:
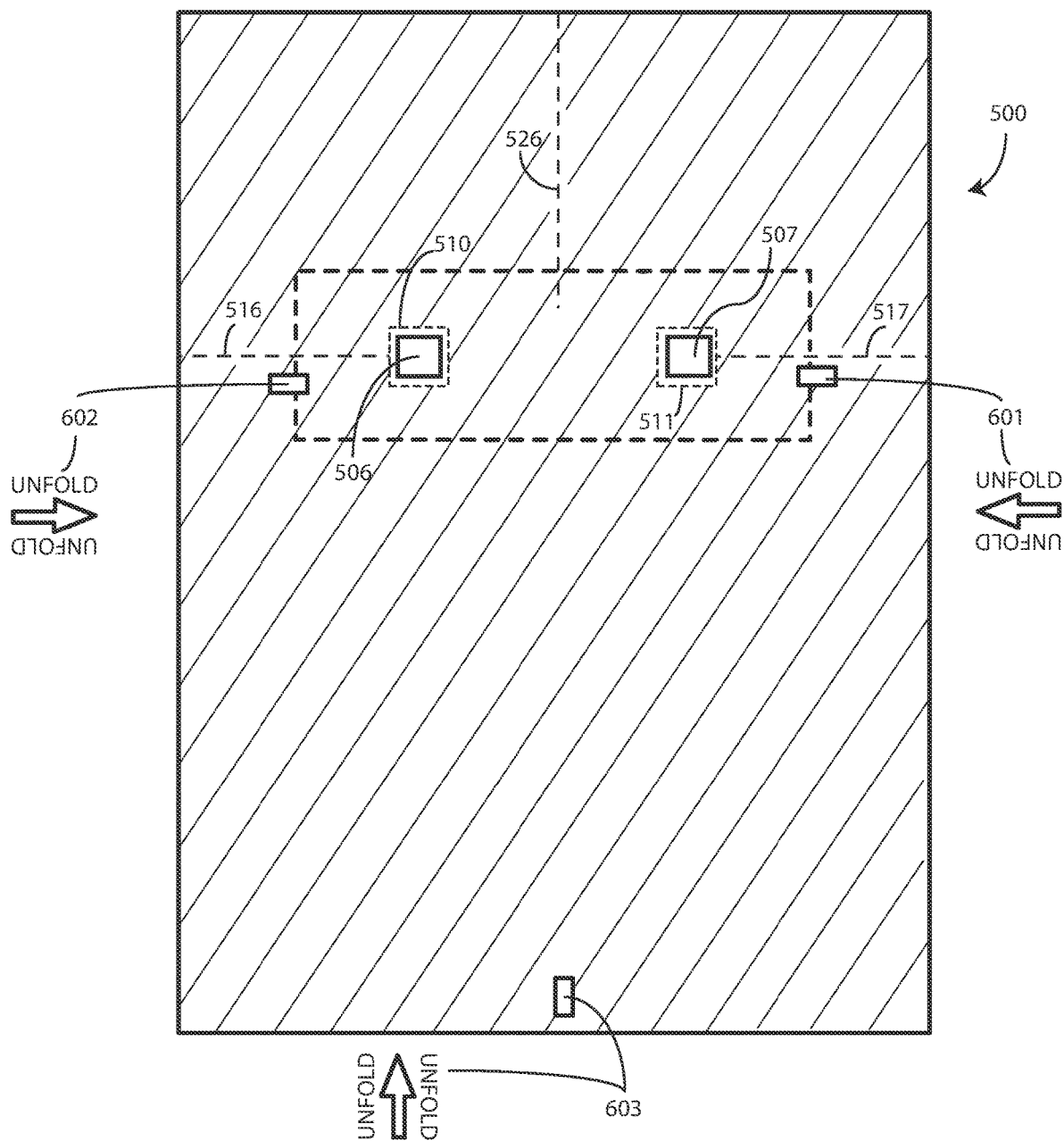
FIG. 6 is a rear view of the medical drape of FIG. 5.

Referring to FIGS. 5 and 6, illustrated therein is another embodiment of a medical drape 500 in accordance with one or more embodiments of the invention. The medical drape 500 is suitable for peripherally inserted central catheter and other medical procedures. FIG. 5 illustrates a front view, while FIG. 6 illustrates a rear view. The rear view of FIG. 6 can be referred to as the "patient side" because it is the side that will contact the patient when the medical drape 500 is used in a procedure.

The illustrative medical drape 500 of FIGS. 5 and 6 is generally rectangular in shape. This illustrative medical drape 500 has a length 501 of about one hundred and twelve inches, plus or minus one and a half inches. The illustrative medical drape 500 has a width 502 of about seventy-five inches, plus or minus one inch. The medical drape 500 can be configured to cover the body of a patient during a procedure.

In one embodiment, the drape material 503 is opaque. In another embodiment, the drape material 503 is transparent. For example, in one embodiment the drape material 503 can be clear 0.05 mm polyethylene sheeting. It should be noted that other clear, flexible materials may be used in place of polyethylene. In another embodiment, the drape material can be manufactured from 45 g spunbond-meltblown-spunbond material. Other materials can be used, as set forth above. The main drape material 503 can generally made of a water-repellent or water-impermeable material and/or is coated with such a water-repellent or water impermeable material to prevent the passage of bodily fluids and/or contaminating microorganisms.

In the illustrative embodiment of FIGS. 5 and 6, the medical drape 500 has two fenestrations 504,505. The fenestrations 504,505 can be configured for placement over a central catheter insertion site. Each fenestration 504,505 can include access ports 506,507 that define openings or apertures in one or more embodiments. In this embodiment, each of the access ports 506,507 is rectangular in shape. In alternative embodiments the fenestration(s) can be generally circular, egg-shaped, oval-shaped, pear-shaped, football-shaped, or the like. It is further contemplated that the drape may have any of the properties described herein, regardless of the shape, number, and/or location of the fenestrations.

The illustrative embodiment of FIGS. 5 and 6, the use of both a first fenestration 504 and a second fenestration 505 provide a "universal" drape that can be used for catheter insertion in either a patient's right or left arm. The medical drape 500 is generally as it would appear after being unfolded and ready for use in a surgical or medical procedure (for example, catheterization, angiography, and radiology). It will be clear to those having benefit of this disclosure that customized "right handed" or "left handed" drapes could be configured with only one aperture. Similarly, expanded usage drapes could be configured with three or more apertures. For example, one drape could have the first fenestration 504, the second fenestration 505, and a third fenestration (not shown) configured for placement over a patient's neck. The fenestrations 504,505, in one embodiment, are configured to allow a peripherally inserted central catheter to be inserted through one of the access ports 507,506 when the medical drape 500 is disposed atop the patient. The fenestrations 504,505 could be configured to accommodate other medical procedures as well.

In one or more embodiments, a single incise film 508 spans both the first fenestration 504 and the first fenestration 504. The single incise film 508 can be combined with an absorptive element that is disposed about the access ports 506,507 as well. In the illustrative embodiment of FIG. 5, the single incise film 508 is substantially rectangular. Where absorptive elements are used with the incise film, they can comprise gauze-like materials, non-woven absorbent materials, or other absorptive materials configured to absorb fluids, such as blood, that may become present during a medical procedure.

In one or more embodiments, to keep the access ports 507,506 closed until needed, release liners 510,511 can be disposed atop the access ports 506,507. In this illustrative embodiment, the release liners 510,511 are rectangular in shape, although other shapes can be used as well. The release liners 510,511 comprise conventional medical release paper affixed to the patient side of the medical drape 500. One suitable means for affixing the release liners 510,511 to the medical drape 500 is with sections of adhesive tape (not shown). The adhesive tape can be a single-coated polyethylene medical tape, such as a medical tape manufactured by 3M (St. Paul, Minn.) as product number 1521.

In the illustrative embodiment of FIGS. 5 and 6, each fenestration 505,504 includes an adhesive tape strip 512,513 as previously described. The adhesive strips 512,513 make removal of the medical drape 500 easier.

The adhesive strips 512,513 of FIGS. 5 and 6 each extend from an opposite edge 514,515 of the medical drape 500 to a corresponding access port 506,507. In this embodiment, the adhesive strips 512,513 are co-linear. In the illustrative embodiment of FIGS. 5 and 6, the adhesive strips 512,513 extends from an opposite edge 514,515 of the medical drape 500, across the single incise film 508 to the access ports 507,506. Each adhesive strip 512,513 includes a corresponding score line 516,517. The score lines 516,517 permit easy tearing of the adhesive tape strip to open the corresponding drape cut. Usage of the fenestrations 504,505 allows the medical drape 500 to be removed without disturbing, for example, a peripherally inserted central catheter that has been placed through one of the access ports 506,507.

In one or more embodiments, to show medical personnel where to begin opening the fenestrations 504,505, indicators 518,519, which are shown in a blown-up view in FIG. 5, can be disposed at the opposite edges 514,515 of the medical drape 500. Said differently, indicators 518,519 can be included to indicate the starting point of each score line 516,517. As noted above, the indicators 518,519 may include instructional indicia such as the words "Tear Here" or "Snap Here." Accordingly, medical personnel knows to grasp and pull apart the indicators 518,519 to tear apart the adhesive tape along the score lines 516,517 to "peel" the drape material 503.

As shown in FIG. 6, other indicators 601,602,603 can be included as well. In this illustrative embodiment, the indicators 601,602,603 are "unfolding indicators" disposed on the rear side of the medical drape 500. The indicators 601,602,603 alert medical personnel regarding how to unfold the medical drape 500 quickly and efficiently. In this embodiment, two indicators 601,602 are oppositely opposed to indicate longitudinal unfolding. A third indicator 603 is oriented substantially orthogonally with the two indicators 602 to indicate lateral unfolding. In one or more embodiments, the medical drape can be folded such that the indicators 601,602,603 become visible in a predetermined order to further instruct medical personnel how to unfold the medical drape. Note that other indicators can be included as well, such as an indicator designating which end is the "head" and an indicator designating which end is the "foot."

Illustrative dimensions now are provided to further describe one embodiment suitable for use in peripherally inserted central catheter applications. It will be clear to those of ordinary skill in the art having the benefit of this disclosure that these dimensions are examples only, provided to present a clearer image of one embodiment, and can readily be modified based upon application or customer demand.

In one embodiment, the width 509 of the incise film 508 is about fifty-three inches, plus or minus one inch. In one embodiment, the length 520 of the incise film 508 is about twenty-three inches, plus or minus one inch. In one embodiment, the fenestrations 504,505 are about eighteen inches apart from each other. In one embodiment, the access ports 506,507 are disposed a distance 521 of about thirty-five inches from a head end 522 of the medical drape 500. In this illustrative embodiment, the access ports 506,507 are configured as rectangles with a width 523 of about six inches and a height 544 of about five inches. The releasable liners 510,511 have corresponding dimensions of ten inches by eleven inches.

As shown in FIGS. 5 and 6 a third adhesive strip 524 is oriented substantially orthogonally with the other adhesive strips 512,513. In this embodiment, the third adhesive strip 524 extends from the incise film 508 to the top end 522 of the medical drape 500. Such an adhesive strip 524 can be useful in opening the medical drape 500 about a patient's face when the patient is completely covered. To assist the medical services provider, another indictor 525 can be placed at the end of the adhesive strip 524 to assist with opening. In this illustrative embodiment, the adhesive strip 524 and its corresponding score line 526 measure about thirty-two inches in length.

Figure 7:
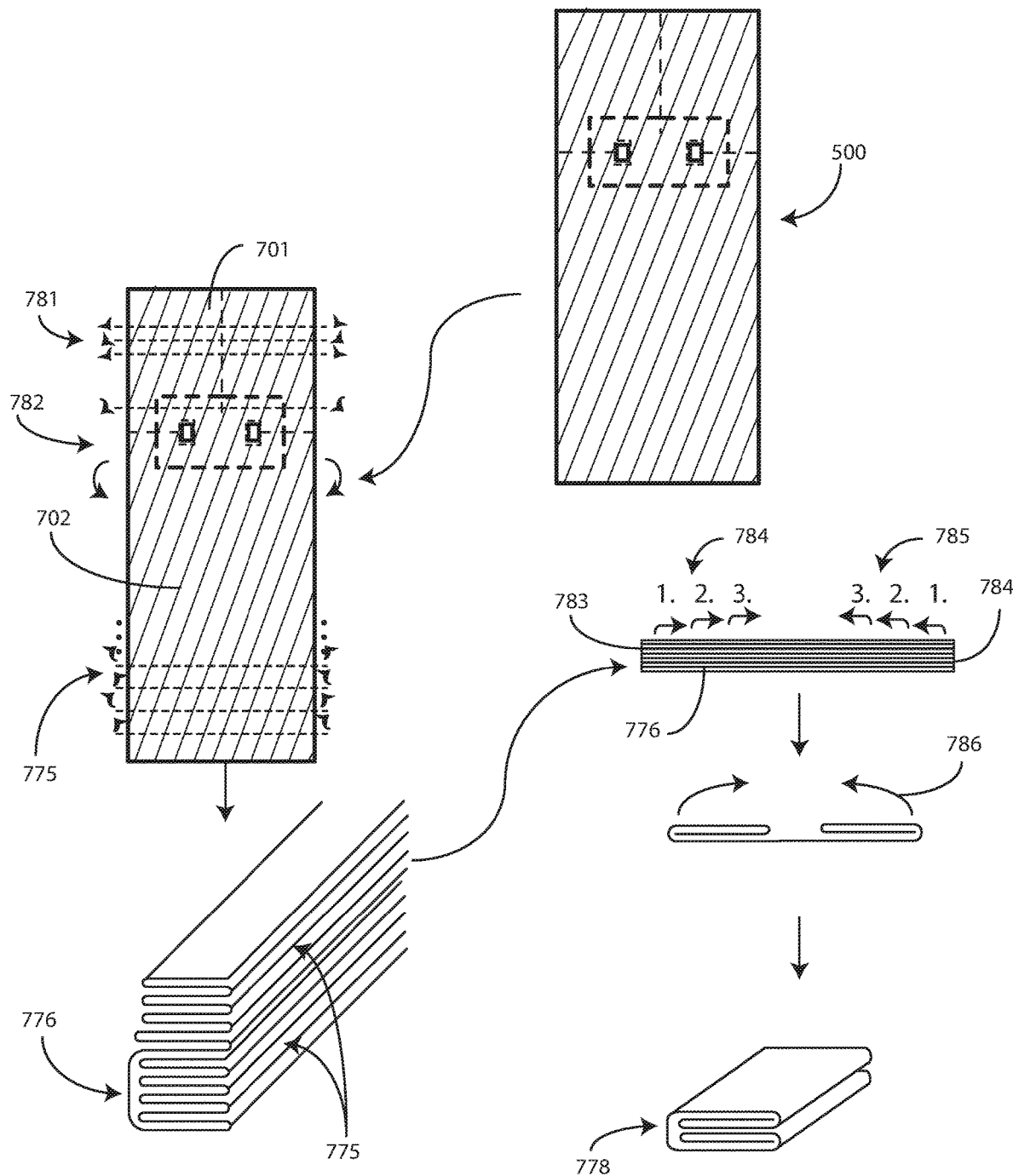
FIG. 7 is a method of folding the medical drape of FIG. 5.

Turning now to FIG. 7, illustrated therein is a method for folding the medical drape 500 shown in FIGS. 5 and 6. The folding method of FIG. 7 facilitates quick, easy, and accurate placement of the medical drape 500 atop a patient prior to a procedure. Moreover, the folding method of FIG. 7 can allow a single person to apply the medical drape 500 during a catheterization or other procedure without compromising an established sterile field required to perform the procedure.

The method of FIG. 7 results in the medical drape 700 being folded in multiple ways: First, the lower portion 702 of the medical drape 500 is folded towards the upper portion 701 with an accordion fold 775. The upper portion 701 is then folded with a second accordion fold 781. An enclosing fold 782 will wrap about the first accordion fold 775, and will also serve as a separator between accordion field 775 and accordion fold 781. This wrap and separate functionality is shown in partially complete pre-folded drape assembly 776. As shown, two stacked accordion folds 775 are separated by the wrapping fold.

From this point, ends 783,784 of the pre-folded drape assembly 776 are folded towards the center of the pre-folded drape assembly 776 with additional rolling folds 784,785. A book fold 786 can then be applied to form folded drape 778. The steps shown in FIG. 7 can be performed by an automated folding machine in an automated environment.

Figure 8:
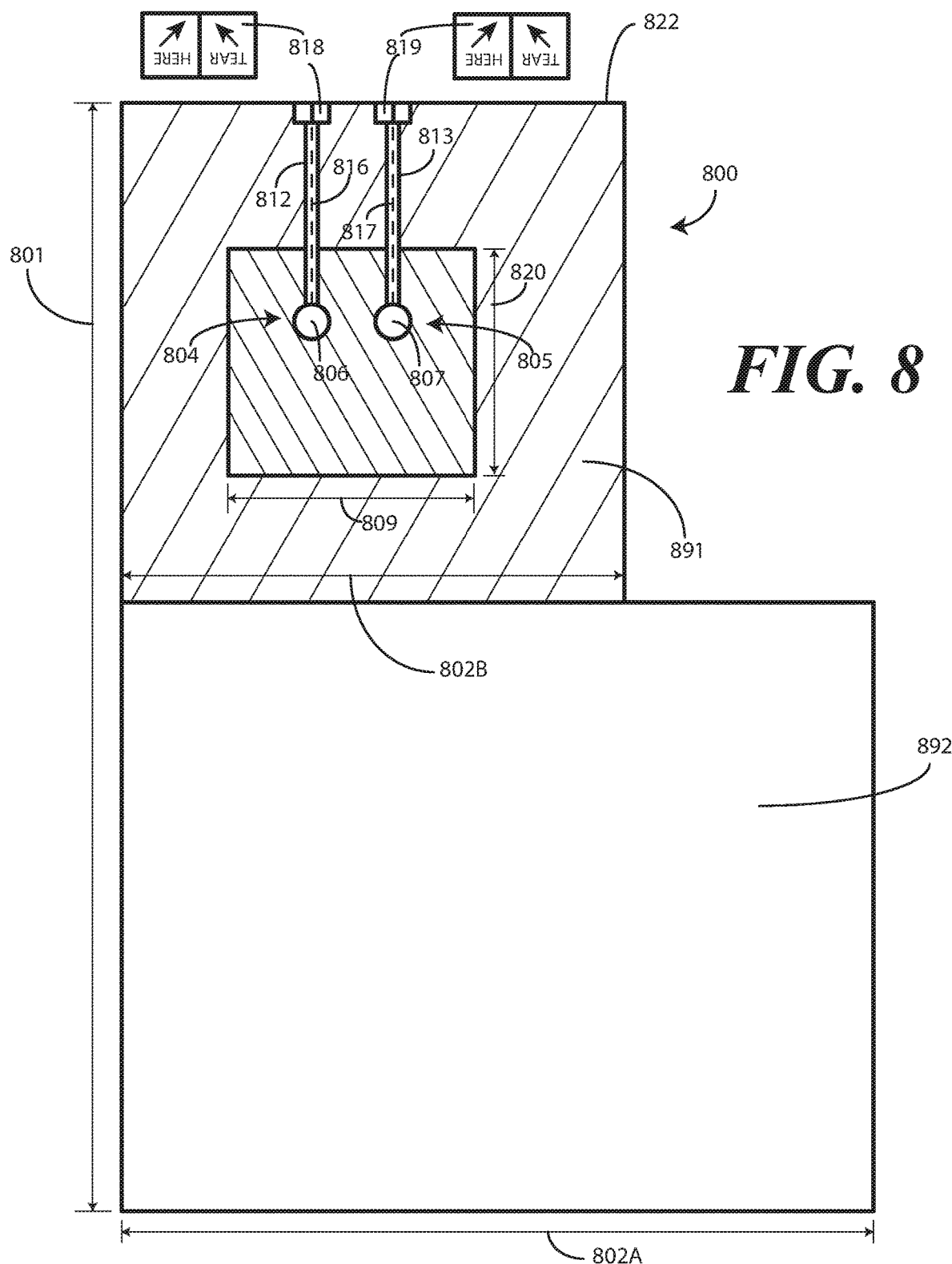
FIG. 8 is a front view of another medical drape according to one embodiment.
Figure 9:
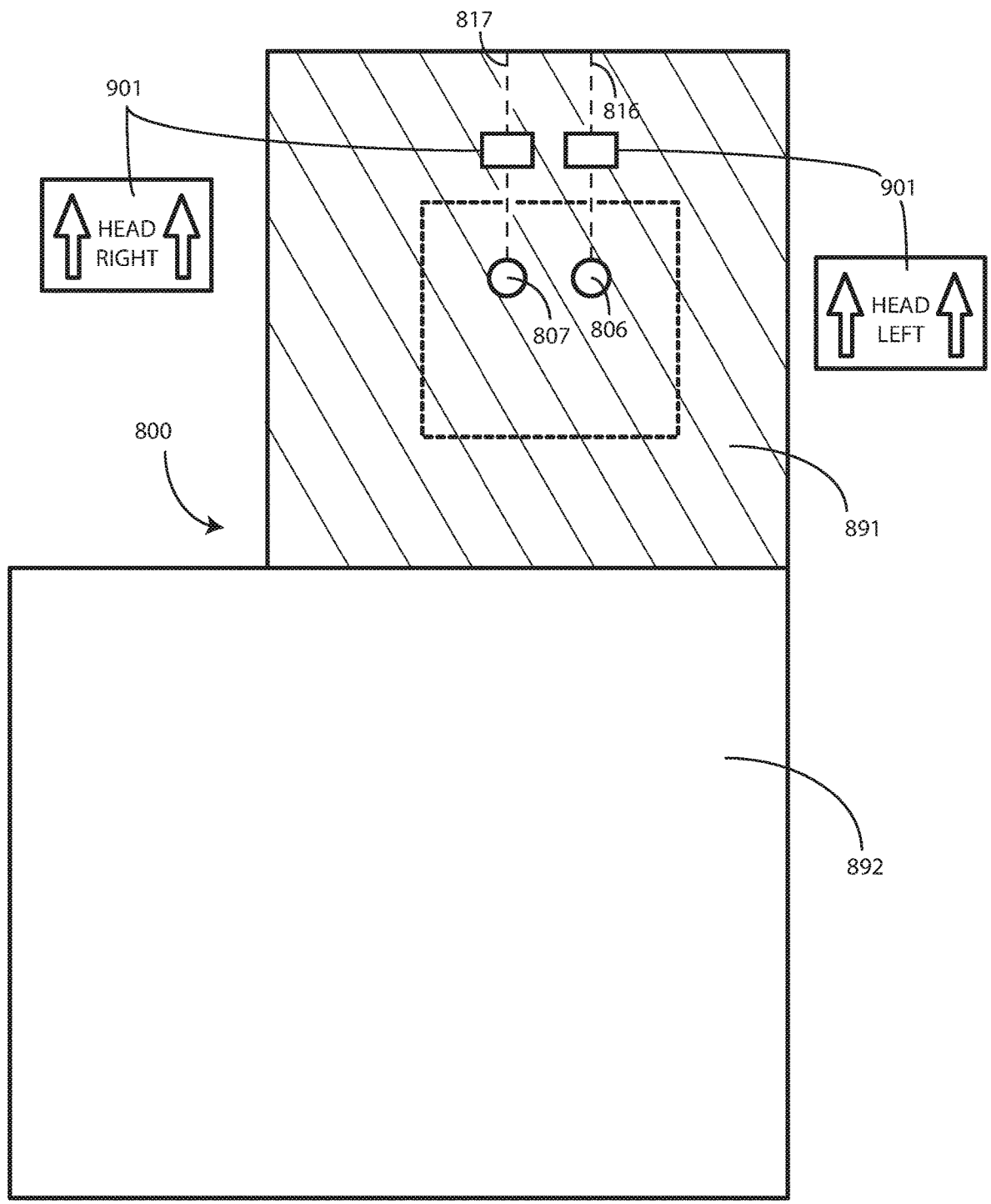
FIG. 9 is a rear view of the medical drape of FIG. 8.

Referring to FIGS. 8 and 9, illustrated therein is another embodiment of a medical drape 800 in accordance with one or more embodiments of the invention. The medical drape 800 is suitable for peripherally inserted central catheter and other medical procedures. FIG. 8 illustrates a front view, while FIG. 9 illustrates a rear view. The rear view of FIG. 9 can be referred to as the "patient side" because it is the side that will contact the patient when the medical drape 800 is used in a procedure.

The illustrative medical drape 500 1 has a "dual rectangle" shape when viewed from the front and rear views, with an upper portion 891 being narrower than the lower portion 892. In one embodiment, the upper portion 891 is configured to be wide enough to cover only arm and a portion of the patient's upper torso. The lower portion 892 can be configured to cover the entire lower torso portions of the patient. Generally, these lower torso portions will be at least inferior to the abdominal portion of the patient. Illustrating by example, the upper portion 891 can be configured for positioning over a brachial portion of a patient, a cubital portion of the patient, an antibrachial portion of the patient, or combinations thereof, while the lower portion 8922 can be configured to cover patient portions inferior thereto.

In one or more embodiments, the upper portion 891 and lower portion 892 are manufactured from different materials. In one embodiment well suited for peripherally inserted central catheters, the lower portion 892 is pellucid while the upper portion 891 is opaque. In another embodiment, the lower portion 892 is transparent, while the upper portion 891 is any of non-transparent, opaque, or non-pellucid. For example, in one embodiment the lower portion 892 can be manufactured from clear 0.05 mm polyethylene sheeting. It should be noted that other clear, flexible materials may be used in place of polyethylene. The upper portion 891 can be manufactured from and opaque material, such as 45 g spunbond-meltblown-spunbond material or the other opaque materials mentioned above.

This illustrative medical drape 800 has a length 801 of about one hundred and forty-nine inches, plus or minus one inch, with the lower portion 892 being about eighty-four inches and the upper portion 891 being about sixty-five inches. The lower portion 892 of this illustrative medical drape 800 has a width 802A of about one hundred and six inches, plus or minus one inch. The upper portion 891 of this illustrative medical drape 800 has a width of about thirty-six inches plus or minus one inch.

In the illustrative embodiment of FIGS. 8 and 9, the medical drape 800 has two fenestrations 804,805. The fenestrations 804,805 can be configured for placement over a central catheter insertion site. Each fenestration 804,805 can include access ports 806,807 that define openings or apertures in one or more embodiments. In this embodiment, each of the access ports 806,807 is round or circular in shape. In alternative embodiments the fenestration(s) can be generally rectangular, egg-shaped, oval-shaped, pear-shaped, football-shaped, or the like. It is further contemplated that the drape may have any of the properties described herein, regardless of the shape, number, and/or location of the fenestrations.

In one or more embodiments, a single incise film 808 spans both the first fenestration 804 and the first fenestration 804. The single incise film 808 can be combined with an absorptive element that is disposed about the access ports 806,807 as well. In the illustrative embodiment of FIG. 8, the single incise film 808 is substantially rectangular. Where absorptive elements are used with the incise film, they can comprise gauze-like materials, non-woven absorbent materials, or other absorptive materials configured to absorb fluids, such as blood, that may become present during a medical procedure.

In the illustrative embodiment of FIGS. 8 and 9, each fenestration 805,804 includes an adhesive tape strip 812,813 as previously described. In this illustrative embodiment, the adhesive tape strips 812,813 are oriented so as to be substantially parallel relative to each other. Each runs from a top end 822 of the upper portion 891 to its corresponding access port 806,807 that is centrally disposed in the upper portion 891.

Each adhesive strip 812,813 includes a corresponding score line 816,817. The score lines 816,817 permit easy tearing of the adhesive tape strip to open the corresponding drape cut. Usage of the fenestrations 804,805 allows the medical drape 800 to be removed without disturbing, for example, a peripherally inserted central catheter that has been placed through one of the access ports 806,807.

In one or more embodiments, to show medical personnel where to begin opening the fenestrations 804,805, indicators 818,819, which are shown in a blown-up view in FIG. 8, can be disposed at the top end 822 of the medical drape 800. Said differently, indicators 818,819 can be included to indicate the starting point of each score line 816,817. As noted above, the indicators 818,819 may include instructional indicia such as the words "Tear Here" or "Snap Here." Accordingly, medical personnel knows to grasp and pull apart the indicators 818,819 to tear apart the adhesive tape along the score lines 816,817 to "peel" the drape material.

As shown in FIG. 9, other indicators 901 can be included as well. In this illustrative embodiment, the indicators 901 are "head side indicators" disposed on the rear side of the medical drape 900. The indicators 901 alert medical personnel regarding how to unfold the medical drape 900 quickly and efficiently, as well as which side of the medical drape should be placed over the right side of the patient and which should be placed over the left side of the patient. In one or more embodiments, the medical drape can be folded such that the indicators 901 become visible in a predetermined order to further instruct medical personnel how to unfold the medical drape. Note that other indicators can be included as well, such as an indicator designating how to unfold the medical drape 800 as well.

Illustrative dimensions now are provided to further describe one embodiment suitable for use in peripherally inserted central catheter applications. It will be clear to those of ordinary skill in the art having the benefit of this disclosure that these dimensions are examples only, provided to present a clearer image of one embodiment, and can readily be modified based upon application or customer demand.

In one embodiment, the width 809 of the incise film 808 is about thirty-six inches, plus or minus one inch. In one embodiment, the length 820 of the incise film 808 is about thirty-two inches, plus or minus one inch. In one embodiment the incise film 808 is disposed about seven inches from the top end 822 of the upper portion 891. In one embodiment, the fenestrations 804,805 are about two and one half inches apart from each other, with each access port 806,807 having a diameter of between one and a half inches and three and a half inches. While not shown in FIGS. 8 and 9, releasable liners can be placed atop the access ports 806,807 as previously described.

Figure 10:
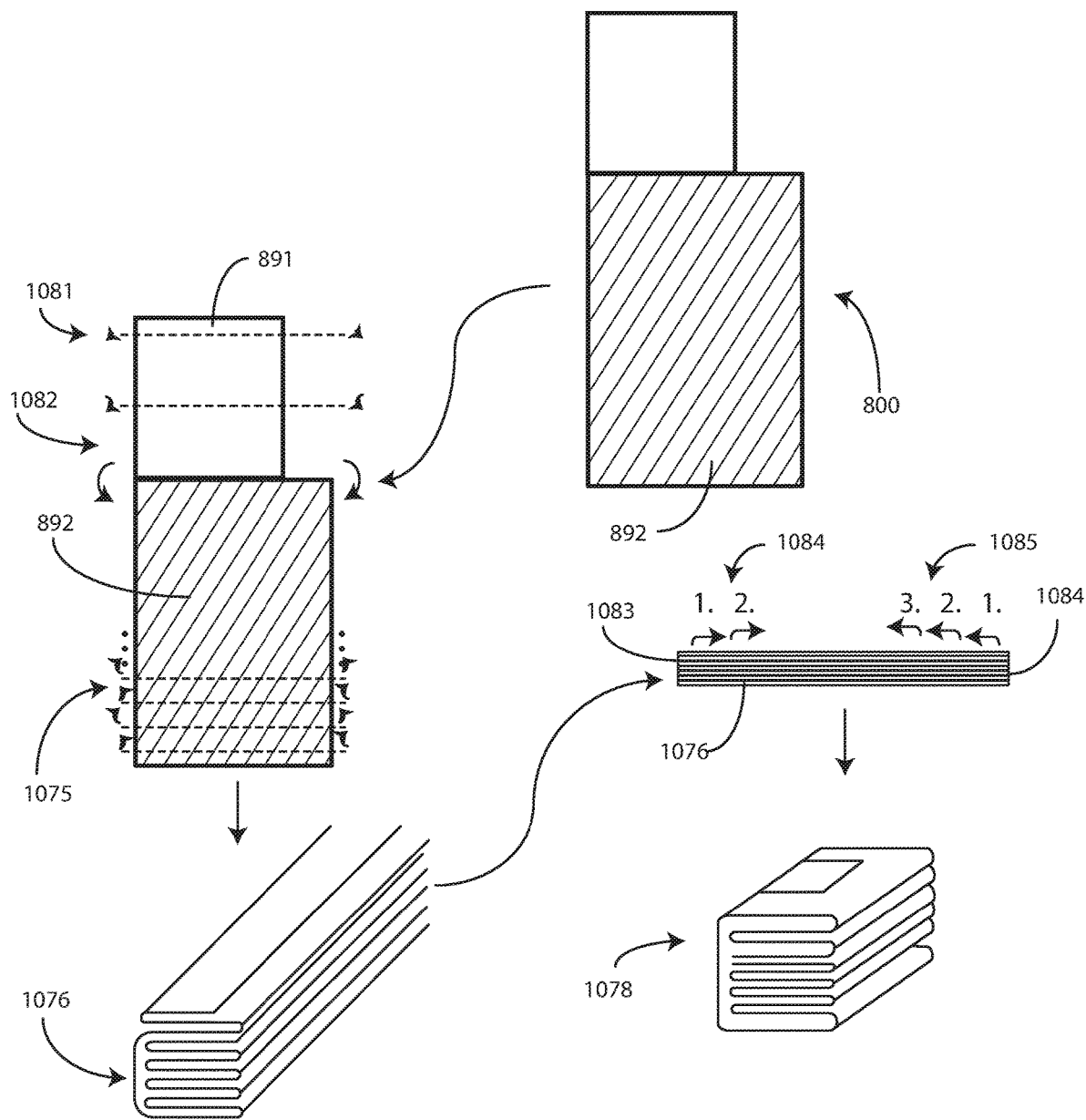
FIG. 10 is a method of folding the medical drape of FIG. 8.

Turning now to FIG. 10, illustrated therein is a method for folding the medical drape 800 shown in FIGS. 8 and 9. The folding method of FIG. 10 facilitates quick, easy, and accurate placement of the medical drape 800 atop a patient prior to a procedure. Moreover, the folding method of FIG.

10 can allow a single person to apply the medical drape 800 during a catheterization or other procedure without compromising an established sterile field required to perform the procedure.

The method of FIG. 10 results in the medical drape 800 being folded in multiple ways: First, the lower portion 892 of the medical drape 800 is folded towards the upper portion 891 with an accordion fold 1075. The upper portion 891 is then folded with a single fold 1081. An enclosing fold 1082 will wrap about the first accordion fold 1075. This wrapping functionality is shown in partially complete pre-folded drape assembly 1076.

From this point, ends 1083,1084 of the pre-folded drape assembly 1076 are folded towards the center of the pre-folded drape assembly 1076 with additional rolling folds 1084,1085. In this embodiment, rolling fold 1085 includes more folds than rolling fold 1084. An asymmetrical book fold 1086 can then be applied to form and asymmetrically book folded drape 1078. The steps shown in FIG. 10 can be performed by an automated folding machine in an automated environment.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claim.

What is claimed is:

1. A medical drape having a tool-less removal feature, the medical drape comprising:
    a drape material having a top side and a back side;
    a first drape cut having a first drape cut starting point at a first exterior edge, a second drape cut having a second drape cut starting point at a second exterior edge opposite the first exterior edge, and a third drape cut oriented substantially orthogonally relative to the first drape cut and the second drape cut, wherein each of the first drape cut and the second drape cut:
        extends completely through a thickness of the drape material such that two adjoining cut edges are completely severed from one another;
        terminates at a corresponding access port;
        comprises an adhesive tape strip positioned along a length of the drape cut, the adhesive tape strip overlapping at least a portion of the drape material on both sides of the drape cut to initially secure the two adjoining cut edges to each other; and
        comprises a scoreline extending along the length of the adhesive tape strip, the scoreline extending only partially through the thickness of the adhesive tape strip to permit easy tearing of the adhesive tape strip for separation of the two adjoining cut edges;
    wherein:
        the medical drape further comprises a single incise film spanning both corresponding access ports; and
        the third drape cut terminates at the single incise film.

2. The medical drape of claim 1, wherein the drape material is arranged with:
    a first side of the drape material comprising a first accordion fold extending toward a center of the drape material;
    a second side of the drape material comprising a second accordion fold extending toward the center of the drape material; and
    at least some of the drape material comprising an enclosing fold disposed about one of the first accordion fold or the second accordion fold to form a semi-folded drape assembly.

3. The medical drape of claim 2, wherein the semi-folded drape assembly is arranged with a third rolling fold and a fourth rolling fold, each extending toward the center of the semi-folded drape assembly.

4. The medical drape of claim 3, wherein the semi-folded drape assembly is further arranged with a book fold to form a folded drape.

5. The medical drape of claim 1, further comprising at least one unfolding indicator attached to the drape material and indicating how to unfold the medical drape.

6. The medical drape of claim 5, further comprising a second unfolding indicator, wherein the first unfolding indicator and the second unfolding indicator are two oppositely opposed folding indicators indicating longitudinal unfolding of the drape material.

7. The medical drape of claim 6, further comprising a third unfolding indicator indicating lateral unfolding of the drape material.

8. The medical drape of claim 1, wherein the drape material is opaque.

9. The medical drape of claim 8, wherein the drape material is manufactured from spunbond-meltblown-spunbond material.

10. The medical drape of claim 1, wherein the drape material is transparent.

11. The medical drape of claim 10, wherein the drape material is manufactured from polyethylene sheeting.

12. The medical drape of claim 1, wherein each of the first drape cut and the second drape cut terminates at a corresponding access port.

13. The medical drape of claim 1, wherein the first drape cut and the second drape cut are arranged in a collinear orientation.

14. The medical drape of claim 1, wherein the single incise film comprises an absorptive material.

15. The medical drape of claim 1, further comprising indicators disposed at a termination of each drape cut.

16. The medical drape of claim 1, wherein the drape material is water-repellant.

17. The medical drape of claim 1, wherein the drape material is water-impermeable.

18. The medical drape of claim 1, wherein a width of the drape material is between seventy-four and seventy-six inches.

19. The medical drape of claim 1, wherein a length of the drape material is between 110.5 inches and 113.5 inches.

20. The medical drape of claim 1, wherein the drape material is rectangular in shape.

* * * * *